US012100488B2

United States Patent
Shiba et al.

(10) Patent No.: US 12,100,488 B2
(45) Date of Patent: Sep. 24, 2024

(54) METHOD AND DEVICE FOR ESTIMATING VALUE TO BE ESTIMATED ASSOCIATED WITH SPECIMEN

(71) Applicant: National Institute for Materials Science, Ibaraki (JP)

(72) Inventors: Kota Shiba, Tsukuba (JP); Ryo Tamura, Tsukuba (JP); Gaku Imamura, Tsukuba (JP); Genki Yoshikawa, Tsukuba (JP)

(73) Assignee: National Institute for Materials Science, Tsukuba (JP)

( * ) Notice: Subject to any disclaimer, the term of this patent is extended or adjusted under 35 U.S.C. 154(b) by 1524 days.

(21) Appl. No.: 16/463,867

(22) PCT Filed: Nov. 21, 2017

(86) PCT No.: PCT/JP2017/041856
§ 371 (c)(1),
(2) Date: May 24, 2019

(87) PCT Pub. No.: WO2018/101128
PCT Pub. Date: Jun. 7, 2018

(65) Prior Publication Data
US 2020/0075134 A1 Mar. 5, 2020

(30) Foreign Application Priority Data

Nov. 29, 2016 (JP) ................................. 2016-230793

(51) Int. Cl.
*G16C 20/70* (2019.01)
*G01N 1/00* (2006.01)
(Continued)

(52) U.S. Cl.
CPC ............... *G16C 20/70* (2019.02); *G01N 1/00* (2013.01); *G01N 19/00* (2013.01); *G01N 29/022* (2013.01);
(Continued)

(58) Field of Classification Search
None
See application file for complete search history.

(56) References Cited

U.S. PATENT DOCUMENTS

2014/0188402 A1* 7/2014 Garcia ............. G01N 33/48792
702/23
2016/0025673 A1 1/2016 Wu

FOREIGN PATENT DOCUMENTS

CN    1381721 A    11/2002
CN    101311711 A    11/2008
(Continued)

OTHER PUBLICATIONS

Bermak, A. et al., "Pattern recognition techniques for odor discrimination in gas sensor array," Encyclopedia of Sensors, vol. 10 (2006) 17 pp. (Year: 2006).*

(Continued)

*Primary Examiner* — Brian M Smith
(74) *Attorney, Agent, or Firm* — Morgan, Lewis & Bockius LLP

(57) ABSTRACT

The present invention provides a method and a device for estimating a value to be estimated associated with a specimen, by performing machine learning of a relationship between a value of an estimation object and an output corresponding thereto, based on an output from a chemical sensor with regard to a plurality of specimens for which specific values to be estimated are known, and using the result of the mechanical learning to estimate a specific value (Continued)

to be estimated on the basis of an output from the chemical sensor with regard to a given unknown specimen.

4 Claims, 37 Drawing Sheets

(51) Int. Cl.

| | | |
|---|---|---|
| *G01N 1/10* | (2006.01) | |
| *G01N 19/00* | (2006.01) | |
| *G01N 29/02* | (2006.01) | |
| *G06N 20/00* | (2019.01) | |
| *G16C 20/20* | (2019.01) | |
| *G16C 20/50* | (2019.01) | |
| *G16C 20/80* | (2019.01) | |
| *G16C 60/00* | (2019.01) | |

(52) U.S. Cl.
CPC .............. *G06N 20/00* (2019.01); *G16C 20/20* (2019.02); *G16C 20/50* (2019.02); *G16C 20/80* (2019.02); *G01N 2001/1087* (2013.01); *G01N 2001/1093* (2013.01); *G16C 60/00* (2019.02)

(56) References Cited

FOREIGN PATENT DOCUMENTS

| | | |
|---|---|---|
| CN | 105283765 A | 1/2016 |
| CN | 105510412 A | 4/2016 |
| CN | 105699463 A | 6/2016 |
| JP | H02-285248 A | 11/1990 |
| JP | H06-160317 A | 6/1994 |
| JP | 2000-292403 A | 10/2000 |
| JP | 2006-275606 A | 10/2006 |
| JP | 2017-156254 A | 9/2017 |
| WO | 2011/148774 A1 | 12/2011 |

OTHER PUBLICATIONS

Schleif, F.-M. et al., "Odor recognition in robotics applications by discriminative time-series modeling," Pattern Analysis Applications vol. 19 (2016) pp. 207-220. (Year: 2015).*

Potyrailo, R., "Sensors in combinatorial polymer research," Macromolecular Rapid Communications, vol. 25 (2004) pp. 77-94. ( Year: 2004).*

Potyrailo, R. et al., "Combinatorial and high-throughput screening of materials libraries: review of state of the art," ACS Combinatorial Science, vol. 13 (2011) pp. 579-633. (Year: 2011).*

Potyrailo, R. et al., "High-throughput analysis: a tool for combinatorial materials science," Springer Science + Business Media (2003) 642 pp. (Year: 2003).*

Office Action issued on Jun. 1, 2021 in European Patent Application No. 17875540.1.

Potyrailo et al., "Dynamic high throughput screening of chemical libraries using acoustic-wave sensor system", Review of Scientific Instruments, vol. 73, No. 3, Mar. 2002 pp. 1277-1283.

Office Action dated Nov. 24, 2021, issued in corresponding European Patent Application No. 17875540.1.

Office Action dated Nov. 15, 2021, issued in corresponding Chinese Patent Application No. 201780067537.1 (with partial translation).

Office Action (with partial translation) dated Jul. 4, 2022 issued in corresponding Chinese Patent Application No. 201780067537.1.

Third Office Action issued on Mar. 8, 2022 in Chinese Patent Application No. 201780067537.1.

Radislav A. Potyrailo and Ralph J. May , "Dynamic high throughput screening of chemical libraries using acoustic-wave sensor system", Review of Scientific Instruments 73, 1277-1283 (2002) https://doi.org/10.1063/1.1448905.

International Search Report issued in corresponding International Patent Application No. PCT/JP2017/041856 dated Feb. 27, 2018.

Potyrailo et al., "Dynamic high throughput screening of chemical libraries using acoustic-wave sensor system," Review of Scientific Instruments, 73: 1277-1283 (2002).

Shiba et al., "Controlled growth of silica-titania hybrid functional nanoparticles through a multistep microfluidic approach," Chemical Communications, 51: 15854 (2015).

Yoshikawa et al., "Nanomechanical Membrane-type Surface Stress Sensor," NANO Letters, 11: 1044-1048 (2011).

Hsieh et al., "Limits of Recognition for Simple Vapor Mixtures Determined with Microsensor Array," Analytical Chemistry, 76: 1885-1895 (2004).

Yongwei et al., "Monitoring storage time and quality attribute of egg based on electronic nose," Analytica Chimica Acta, 650: 183-188 (2009).

Barbri et al., "An electronic nose system based on a micro-machined gas sensor array to assess the freshness of sardines," Sensors and Actuators B: Chemical, 141: 538-543 (2009).

Lee et al., "Temperature modulation in semiconductor gas sensing", Sensors and Actuators B, 60 (1999) 35-42.

Extended European Search Report dated Sep. 1, 2020, issued in corresponding European Patent Application No. 17875540.1.

Office Action issued on Feb. 26, 2021 in Chinese Patent Application No. 201780067537.1 (with partial translation).

* cited by examiner

FIG. 12E

| Ultrapure water | Commercial water | Tap water | PBS | Green tea | Oolong tea | Shochu & green tea |
|---|---|---|---|---|---|---|
| Beer | Shochu & Oolong tea | Sangria | Umeshu | Red wine | Ryorishu | Mirin |
| Japanese sake | Shokoshu | Shochu (barley) | Cassis liqueur | Shochu (plant worm) | Shochu (sweet potatoes) | Vodka |
| Gin | Palinka | Rum | Brandy | Whisky | Water/EtOH (95/5) | Water/EtOH (90/10) |
| Water/EtOH (85/15) | Water/EtOH (80/20) | Water/EtOH (75/25) | Water/EtOH (70/30) | Water/EtOH (65/35) | Water/EtOH (60/40) | Water/EtOH (55/45) |

FIG. 13E

| Ultrapure water | Beer | Sangria | Umeshu | Red wine | Ryorishu | Mirin |
|---|---|---|---|---|---|---|
| Japanese sake | Shokoshu | Shochu (barley) | Cassis liqueur | Shochu (plant worm) | Shochu (sweet potatoes) | Vodka |
| Gin | Palinka | Rum | Brandy | Whisky | Water/EtOH (80/20) | Water/EtOH (60/40) |

FIG. 14C

| Ultrapure water | Beer | Sangria | Umeshu | Red wine | Ryorishu | Mirin |
|---|---|---|---|---|---|---|
| Japanese sake | Shokoshu | Shochu (barley) | Cassis liqueur | Shochu (plant worm) | Shochu (sweet potatoes) | Vodka |
| Gin | Palinka | Rum | Brandy | Whisky | Water/EtOH (80/20) | Water/EtOH (60/40) |

FIG. 16C

| Ultrapure water | Commercial water | Tap water | PBS | Green tea | Oolong tea | Shochu & green tea |
|---|---|---|---|---|---|---|
| Beer | Shochu & Oolong tea | Sangria | Umeshu | Red wine | Ryorishu | Mirin |
| Japanese sake | Shokoshu | Shochu (barley) | Cassis liqueur | Shochu (plant worm) | Shochu (sweet potatoes) | Vodka |
| Gin | Palinka | Rum | Brandy | Whisky | Water/EtOH (95/5) | Water/EtOH (90/10) |
| Water/EtOH (85/15) | Water/EtOH (80/20) | Water/EtOH (75/25) | Water/EtOH (70/30) | Water/EtOH (65/35) | Water/EtOH (60/40) | Water/EtOH (55/45) |

METHOD AND DEVICE FOR ESTIMATING VALUE TO BE ESTIMATED ASSOCIATED WITH SPECIMEN

TECHNICAL FIELD

The invention relates to a method and a device for estimating an estimation target value associated with a specimen and specifically relates to a method and a device for implementing the estimation using machine learning. Herein, the estimation target value may be a physical quantity of a specimen such as the concentration of a specific component contained in the specimen or may be a quantity which is a combination of some physical or other quantities, instead of a simple physical quantity. Alternatively, the estimation target value may be any abstract or sensory quantity associated with the specimen.

BACKGROUND ART

Progressing development in chemical sensors such as Membrane-type Surface stress Sensors (MSS) (Patent Literature 1) and receptors where their physical quantity changes due to adsorption of various chemical substances or the like thereto has facilitated detecting a wide variety of chemical substances and the like.

Most analytes contain multiple or often numerous different components irrespective of whether the analytes exist in nature or are produced artificially. A chemical sensor individually responds to such multiple components of the measured specimen. The signal obtained from the chemical sensor therefore is composed of superimposed signals based on the multiple components. For example, odor is composed of thousands of chemical substances of different concentrations. It is still difficult to extract specific information from odor although various analyses based on odor have been performed since ancient times.

Quantification is an important process in most analyses. Many quantification methods have been developed for centuries to accurately obtain a characteristic value of a measuring target. Representative values to be obtained are volume, weight, density, concentration, and the like, for example. There are many methods available for measuring these values now. However, in many of such methods, the object needs to be composed of a single component, or at least the target component to be measured needs to be analyzed independently of the other components. Therefore, chromatography or the like is normally used to separate individual components from a complicated mixture for quantification of each component.

According to such a method, in order to analyze a specimen containing a lot of various components by using a sensor having the property of responding to multiple types of chemical substances, it is necessary to perform multiple steps of processing, including: first isolating a component to be detected, from the specimen; and then supplying the isolated component to the sensor. Such analyses require long time and also require expensive equipment, such as a chromatography apparatus for isolation and the like. Furthermore, with such a method, it is often difficult to address the demand for analyses at the site where the specimen is obtained or therearound.

CITATION LIST

Patent Literature

Patent Literature 1: WO 2011/148774

Non Patent Literature

Non-patent Literature 1: G. Yoshikawa, T. Akiyama, S. Gautsch, P. Vettiger, and H. Rohrer, "Nanomechanical Membrane-type Surface Stress Sensor", Nano Letters 11, 1044-1048 (2011).
Non-patent Literature 2: Shiba, K., Sugiyama, T., Takei, T. & Yoshikawa, G. "Controlled growth of silica-titania hybrid functional nanoparticles through a multistep microfluidic approach", Chem. Commun. 51, 15854-15857, doi: 10.1039/C5CC07220A (2015).
Non-patent Literature 3: Hsieh, M.-D. & Zellers, E. T. "Limits of Recognition for Simple Vapor Mixtures Determined with a Microsensor Array", Anal. Chem. 76, 1885-1895, doi:10.1021/ac035294w (2004).
Non-patent Literature 4: Wang Yongwei, Jun Wang, Bo Zhou, Qiujun Lu, "Monitoring storage time and quality attribute of egg based on electronic nose" Analytica Chimica Acta 650 (2009) 183-188.
Non-patent Literature 5: N. El Barbri, J. Mirhisse, R. Ionescu, N. El Bari, X. Correig, B. Bouchikhi, E. Llobet, "An electronic nose system based on a micro-machined gas sensor array to assess the freshness of sardines" Sensors and Actuators B 141 (2009) 538-543.

SUMMARY OF INVENTION

Technical Problem

A problem of the invention is to facilitate a quantitative analysis for a specific chemical substance in a specimen to be measured which possibly contains multiple chemical substances even by using a sensor that responds to the multiple chemical substances. On a larger level, the problem of the invention is to use an output from a chemical sensor to estimate an estimation target which may be a complicated, abstract, or another indirect quantity that cannot be directly obtained by measuring the specimen.

Solution to Problem

According to an aspect of the invention, a method of estimating an estimation target value associated with a specimen is provided, the method comprising: performing machine learning for a relationship between a values of a specific estimation target and an output of a chemical sensor corresponding thereto based on output of the chemical sensor for a plurality of specimens the values of the specific estimation target of which are known, and estimating the value of the specific estimation target using a result of the machine learning based on an output of the chemical sensor in response to a given unknown specimen.

Herein, the output to be learnt may be values at time points selected from the entire output.

The output to be learnt may be a group of values obtained by performing a predetermined operation using the output.

A plurality of chemical sensors may be used as the chemical sensor where the responses of the plurality of the chemical sensors are different each other in response to at least one of the components that may be contained in the unknown specimen.

The amount of each of the specimen given to the chemical sensor may be varied in time.

The time variation may be a periodic variation.

The estimation target may be a physical quantity of the specimen.

The physical quantity may be a concentration of a specific component in the specimen.

According to another aspect of the invention, an apparatus for estimating an estimation target value associated with a specimen is provided, comprising: a chemical sensor to which a specimen is introduced, wherein the value of the estimation target of the specimen is estimated based on a response from the chemical sensor by using any one of the aforementioned methods is used.

Advantageous Effect of Invention

According to the invention, it is possible to estimate values of various estimation targets of a specimen based on a chemical sensor output, specifically, to analyze a specimen which possibly contains multiple chemical substances and easily measure and estimate the quantity of a specific component contained in the specimen.

BRIEF DESCRIPTION OF DRAWINGS

FIG. 4 illustrates plots of all possible combinations of three principal components together with a 3D plot based on the three principal components. The PCA herein was performed using four parameters extracted from the last three response cycles in the measured responses illustrated in FIGS. 11A to 11D. The first and second responses are omitted because an elapse of a certain period of time is necessary to obtain stable reproducible responses. The parameter extraction is illustrated in FIG. 6 in detail.

In FIG. 8, lower diagrams illustrate parity plots of predicted alcohol concentration (on the vertical axis, denoted by Prediction %) vs real alcohol concentration (on the horizontal axis, denoted by Real %) in an atmospheric environment. The small gray circles represent known alcoholic beverages used to train the machine learning model. The small black circles represent unknown alcoholic beverages (red wine (12%), sweet potato shochu (25%), and whiskey (40%)).

FIG. 12E is a diagram illustrating the liquid specimens corresponding to the 35 graphs in each of FIGS. 12A to 12D.

FIG. 13E is a diagram illustrating the liquid specimens corresponding to the 21 graphs in each of FIGS. 13A to 13D.

FIG. 14C is a diagram illustrating the liquid specimens corresponding to the 21 graphs in each of FIGS. 14A and 14B.

FIG. 16C is a diagram illustrating the liquid specimens corresponding to the 35 graphs in each of FIGS. 16A and 16B.

DESCRIPTION OF EMBODIMENTS

Figure 1:
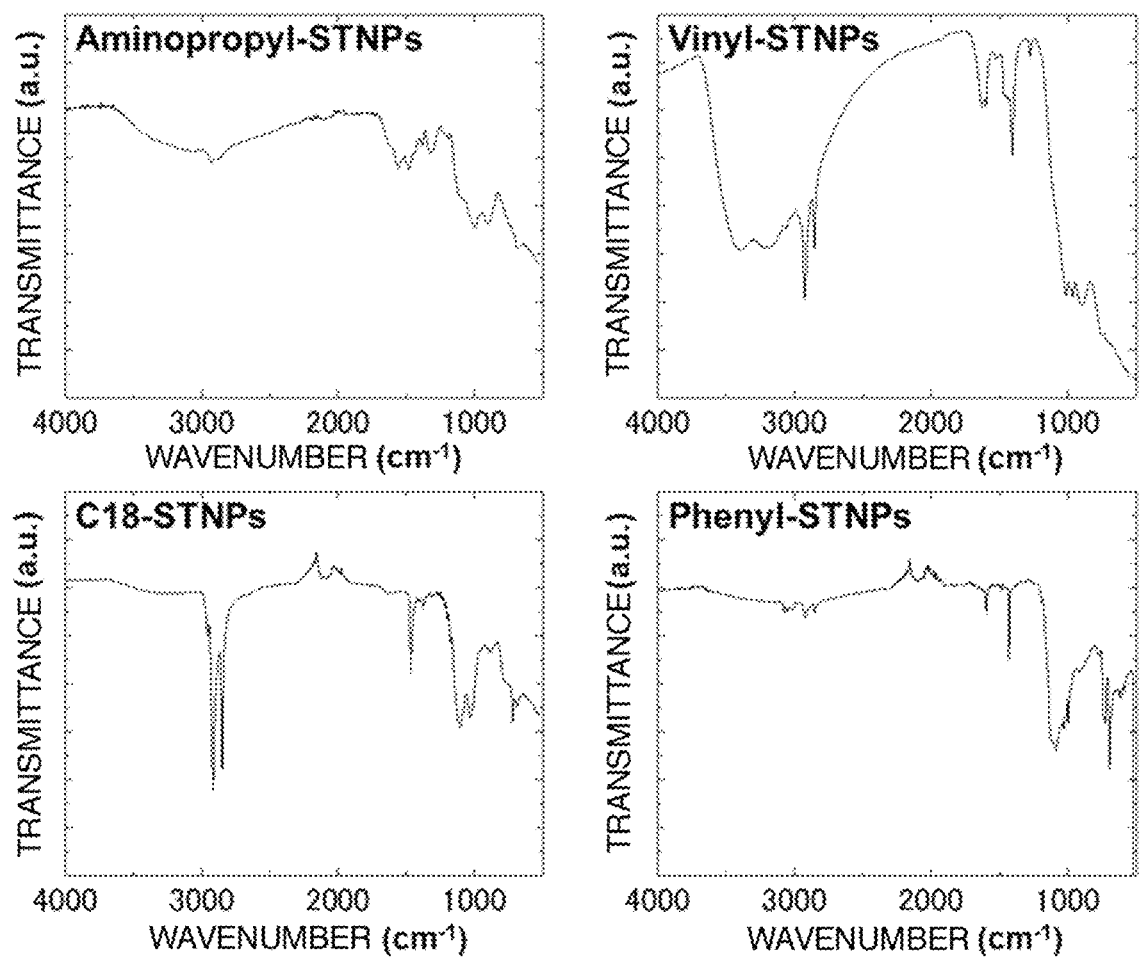
FIG. 1 is a diagram illustrating diagrams of FT-IR spectra of the four types of nanoparticles (Aminopropyl-STNPs, Vinyl-STNPs, C18-STNPs, and Phenyl-STNPs) used in Examples of the invention.

In an aspect of the invention, based on response signals from a chemical sensor to multiple specimens including the estimation target (such as the concentration) of which is already known of a specific component (hereinafter, also referred to as a chemical substance), for example, machine learning is performed to obtain the relationship between the concentration of the chemical substance and the response signals to the specimen. Next, a specimen (unknown specimen) the concentration of the specific chemical substance of which is desired to be obtained is given to the chemical sensor. Using the response signal to the specimen, the concentration of the unknown specimen is estimated based on the results of the machine learning. The invention is not limited to concentration estimation and is applicable to estimation of values of any estimation target correlating with outputs of the chemical sensor. The estimation target may be a physical quantity of a specific component different from the concentration or may be an object more complex, abstract, or sensory. For example, substances, such as gas or liquid, which are emitted from an organism are measured with a chemical sensor while evaluation values concerning the health conditions of the organism are incorporated for machine learning. This enables estimation of the health conditions of an unknown organism from substances emitted from the same. Besides the organism, machine learning is performed for measurement outputs of emissions from a machine, such as an internal combustion engine, through a chemical sensor and the normality of the operation of the machine. This enables automatic and overall estimation and evaluation concerning the machine conditions. As a sensory estimation target, machine learning for smells and discomfort enables automatic measurement and evaluation of stink in various situations without a human trained for smell evaluation. In the following description, the estimation target is the concentration of a specific component in specimens by way of example. It is obvious to those skilled in the art that this does not cause loss of generality. General theories of machine learning have been variously studied in the informatics and statistics field, and the results thereof are known widely. Examples of this application are described using kernel ridge regression as a non-limiting example of various types of machine learning methods. However, it is certain that other machine learning methods can be properly used.

Herein, to implement more accurate estimation, the aforementioned known and unknown specimens may be supplied to multiple chemical sensors which are different in responses to each chemical substance, for machine learning based on the response signals from the multiple chemical sensors.

Machine learning may be performed for all response signals from a chemical sensor in principle. However, this yields a huge amount of data to be processed in many cases. Instead of supplying all response signals to machine learning, only informative part of response signals (characteristic part that greatly varies with a difference between specimens) or in addition thereto, reference part to extract values of response signals may be selected for machine learning. This can significantly reduce the amount of calculation with little degradation in accuracy of machine learning. Furthermore, machine learning may be performed based on a group of values obtained by performing a predetermined operation for the selected parts described above, not based on the selected parts themselves. Examples of "a group of values obtained by performing a predetermined operation" herein include, not limited thereto, signal inclination, differential values, integral values, response times, values obtained by fitting with a particular function, values obtained through various conversions, such as Fourier transform, or those values calculated using signals from a different channel or from another sensor. The values (feature quantities, explanatory variables) supplied to machine learning can be various types of values. Furthermore, the values supplied to machine learning may be any model composed of various functions.

As a specific example of selection of characteristic part or reference part of response signals, in Examples, a specimen to be measured and carrier gas were alternately supplied in square wave form, and the response signal thereto was used to perform machine learning and estimation based on the results thereof. When the specimen is not gas but liquid, properly selected liquid is used instead of carrier gas. Hereinafter, a description is given of the case of gas without loss of generality. The response signal in this case was basically periodic signal. Some characteristic points were selected in each period, and the values of those points or the occurrence times thereof, if necessary, were combined to calculate some parameters. Based on these parameters, machine learning was performed. Limiting the method of selection to the method described in Examples is not intended. It is possible to properly select suitable points in accordance with the way of supplying specimens to a chemical sensor, the properties of the employed chemical sensor, and the like.

The flow rate of the specimen supplied to a chemical sensor is varied with time by alternate switching of the flow of the specimen supplied to the chemical sensor as described above (or by giving a proper change to the flow of the specimen in a different way) to detect a dynamic behavior of the chemical sensor in response to the chemical species to be detected in the specimen. Alternatively, if sufficient information can be obtained by detecting comparatively static behavior of the chemical sensor, it is unnecessary to perform alternate switching or the like.

Chemical sensors used in Examples were Membrane-type Surface stress Sensors (MSS) (Patent Literature 1, Non-patent Literature 2), which are a kind of nanomechanical sensors. In an MSS, a sensitive membrane (also referred to as a receptor layer) applied on a membrane supported at multiple places on the circumference absorbs a supplied specimen and swells to produce stress. The stress is then detected through piezoresistors as a sensor signal. MSS was employed herein because MSS has useful characteristics, including higher sensitivity and higher stability than those of cantilever-type sensors conventionally proposed.

Responses from MSS are determined by interaction between a specimen (various chemical substances in the specimen) and the receptor layer. The interaction includes adsorption and desorption of the specimen and expansion and contraction of the receptor layer due to the same. Such expansion and contraction or the like differ depending on chemical substances adsorbed on or desorbed from the receptor layer. Using the matter that such differences depend on the material, structure, and the like of the receptor layer enables estimation based on the aforementioned machine learning technique. Needless to say, many types of chemical sensors are known, in addition to MSS. It is therefore possible to properly use another chemical sensor instead of MSS. Furthermore, the receptor layer of the MSS was mainly composed of nanoparticles modified with various types of functional groups in Examples. It is certain that the sensitive membrane is not limited to such a form. It may include various materials and structures, including a receptor layer of a homogeneous structure (a coating of polymers not containing particulate matters, for example).

The following description illustrates that the concentration of a specific chemical substance in a specimen containing many types of (or often unknown) chemical substances can be quantitatively measured by using an assembly of multiple MSS (hereinafter, sometimes referred to as a sensor array) and combining the same with machine learning. As an example of the specimen and specific chemical substance, the alcohol concentration of an alcoholic beverage is employed. Gas (often called "odor") obtained by evaporation from liquid specimens is used to estimate the alcohol concentrateion of the original liquid specimen. However, in the following description, it is obvious that those specimens and chemical substances to be measured are just illustrated by way of example and other various types of specimens and chemical substances can be arbitrarily selected.

Examples

[Preparation of Silica/Titania Hybrid Nanoparticles with Various Surface Functionalities]

Two alkoxides, that is, titanium tetraisopropoxide (TTIP) and various types of silane coupling agent, were combined with a multi-step microfluidic method for hydrolysis and co-condensation reaction (described in detail later), thus producing silica/titania hybrid nanoparticles (NPs) modified with various types of surface functional groups (hereinafter, also just referred to as nanoparticles). In Examples, four types of functional groups including aminopropyl, vinyl, octadecyl, and phenyl groups (denoted by Aminopropyl, Vinyl, C18, and Phenyl in the drawings and tables, respectively) were immobilized on nanoparticle surfaces. To confirm the presence of those functional groups on the nanoparticle surfaces, the nanoparticles were characterized by FT-IR spectroscopy, and the results illustrated in FIG. 1 were thereby obtained. The FT-IR spectra illustrated in FIG. 1 reveal the presence of those four types of functional groups.

The FT-IR spectra in FIG. 1 are individually described briefly. The FT-IR spectrum of the vinyl group-modified nanoparticles (Vinyl-STNPs) shows two characteristic absorption bands at 1406 cm-1 and 1600 $cm^{-1}$. The former is attributed to —$CH_2$ in-plane bending deformation while the latter is attributed to the C═C stretching mode. The FT-IR spectrum of the octadecyl group-modified nanoparticles (C18-STNPs) shows very strong absorption at 2848 $cm^{-1}$ and 2916 $cm^{-1}$. This is attributed to the C—H stretching vibration of octadecyl groups. The absorption bands appearing at 1430 $cm^{-1}$ and 738 $cm^{-1}$ following those absorption bands are attributed to phenyl groups covalently bonded to Si. The absorption bands appearing at 1954 $cm^{-1}$, 1571 $cm^{-1}$, 1490 $cm^{-1}$, 1067 $cm^{-1}$, 1027 $cm^{-1}$, and 694 $cm^{-1}$ are attributed to vibration modes of phenyl groups themselves. As for the aminopropyl group-modified nanoparticles (Aminopropyl-STNPs), the FT-IR spectrum thereof illustrated in FIG. 1 well corresponds to the spectrum reported before in Non-patent Literature 2, indicating that the nanoparticles were properly functionalized with aminopropyl groups. As for C18-STNPs and the phenyl group-modified nanoparticles (Phenyl-STNPs), there are very few absorption bands that exhibit the properties of the hydrogen bond network around 3000 to 3500 $cm^{-1}$. This reflects the hydrophobicity specific to these functional groups. In contrast, as for Aminopropyl-STNPs and Vinyl-STNPs, clear absorption bands appear in the same wavenumber region. It is known that the FT-IR spectrum of solid modified with aminopropyl groups has the same tendency because of the hydrophilic surface properties. However, solid functionalized with vinyl groups is basically considered to be hydrophobic. Taking into consideration of the quantity of immobilized vinyl groups determined by a thermogravimetric analysis, it is concluded that a lot of accessible hydroxyl groups still remain, exhibiting hydrophilicity.

Figure 2:
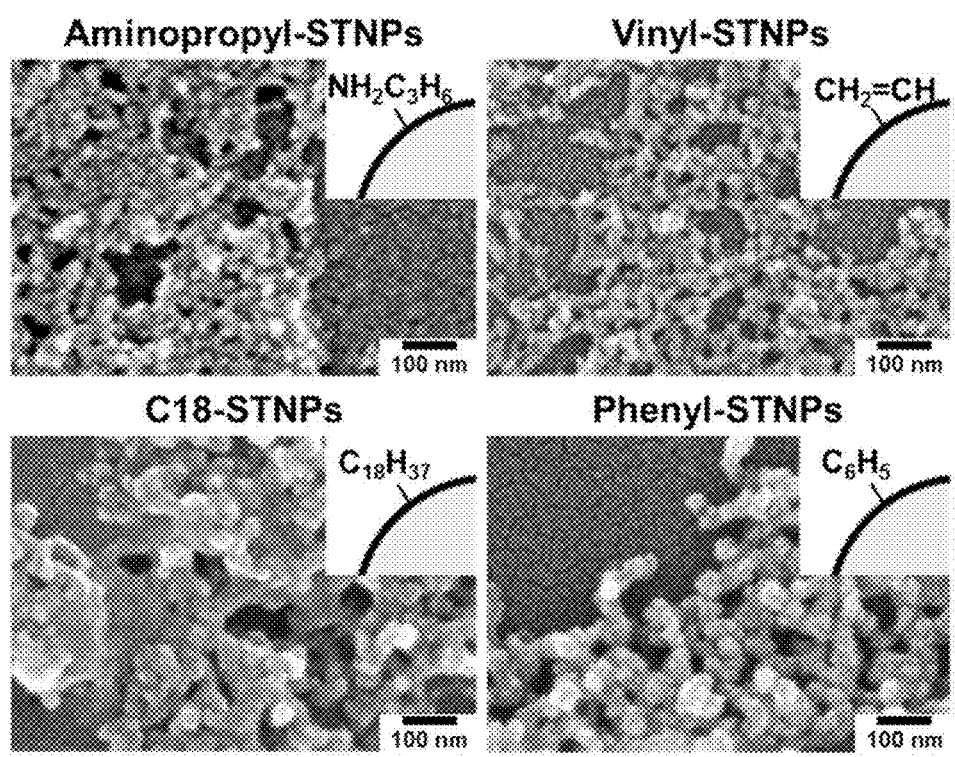
FIG. 2 illustrates SEM images of the four types of nanoparticles used in Examples of the invention.

SEM images illustrated in FIG. 2 reveal that these four types of nanoparticles have an average size of several tens nm. It is proper to call these four particles 'nanoparticles (NPs)'. The size distributions are narrow enough, and it is concluded that any by-product was not formed because of uniform nucleation accompanying the reaction between TTIP and a silane coupling agent and the subsequent growth. This shows that the silane-based functional groups are co-precipitated with titania to form functionalized NPs. The nanoparticles herein which are surface-functionalized with the functional groups are expressed as [functional group name]-STNPs (Aminopropyl-STNPs and the like).

[Detection Properties Under Atmospheric Conditions of MSS Coated with Various Types of NPs]

Figure 10:
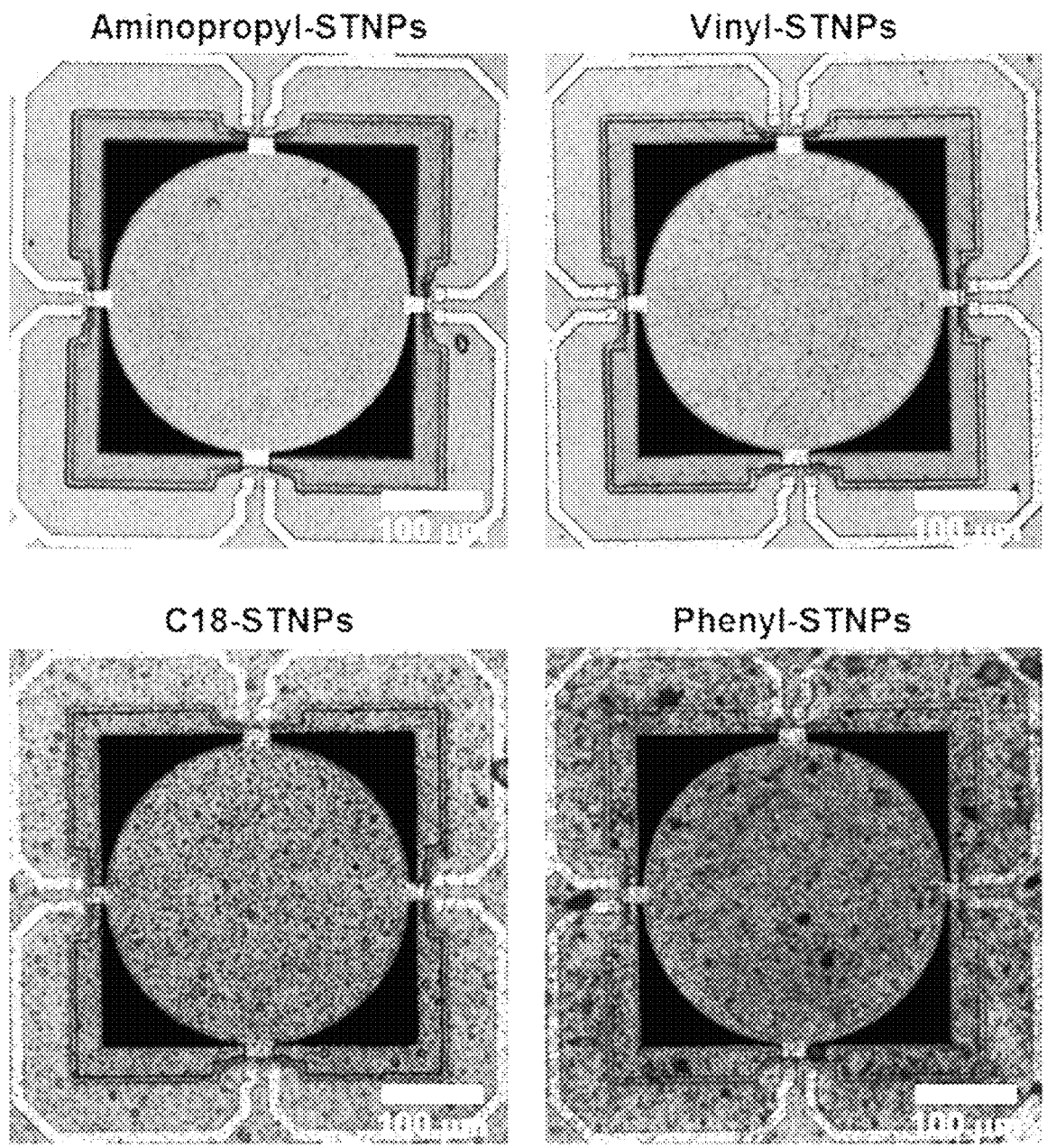
FIG. 10 illustrates optical microscopic images of MSS coated with the four types of nanoparticles (Aminopropyl-STNPs, Vinyl-STNPs, C18-STNPs, and Phenyl-STNPs).
Figure 11A:
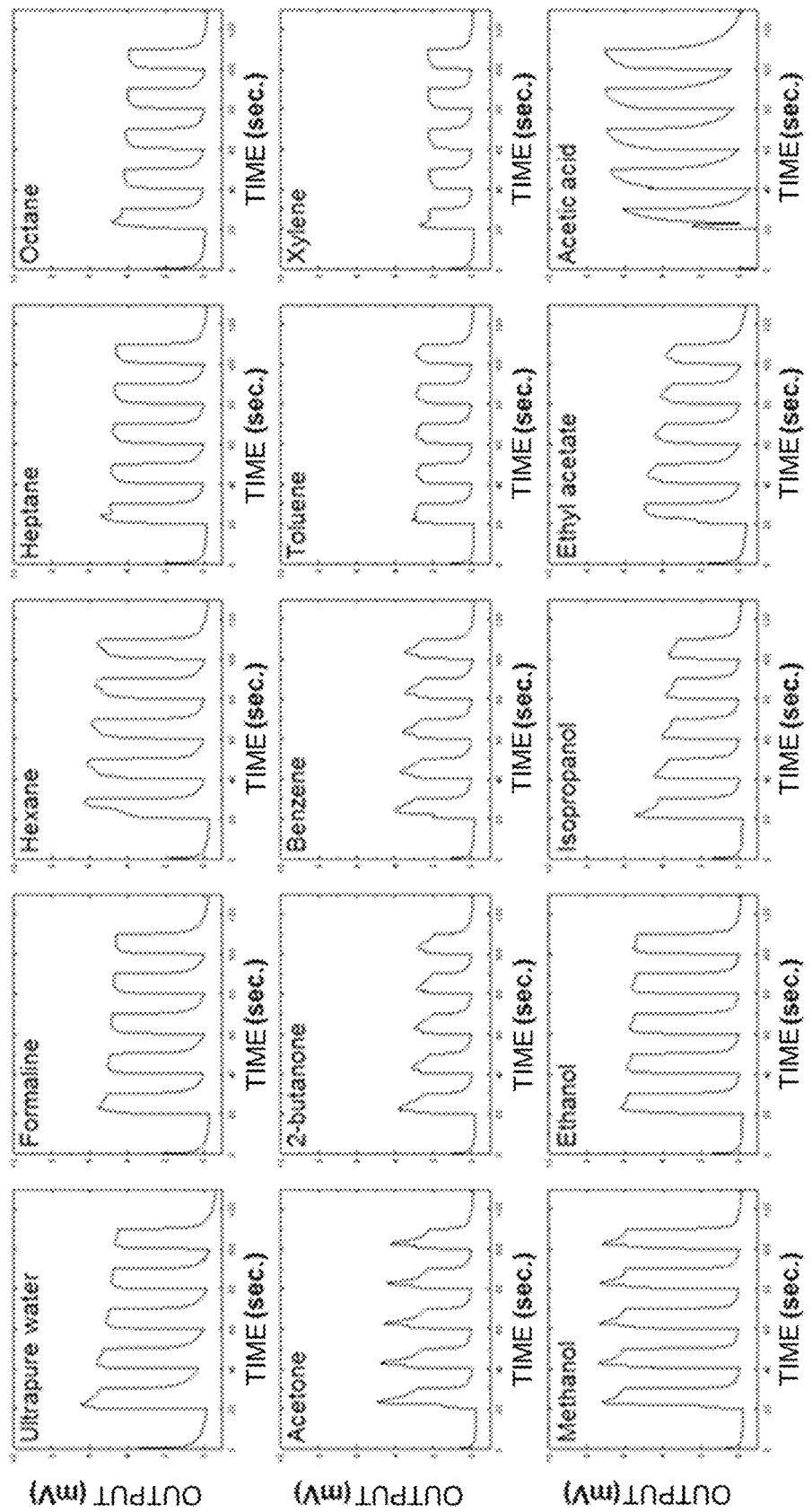
FIG. 11A is a diagram illustrating responses of Aminopropyl-STNPs-coated MSS to 15 types of chemical substances. The names of the chemical substances are written at the top of each graph. The numerical values on the horizontal axis of each graph are 0, 20, 40, 60, 80, 100, and 120 while the numerical values on the vertical axis are 0, 2, 4, 6, 8 and 10.
Figure 11B:
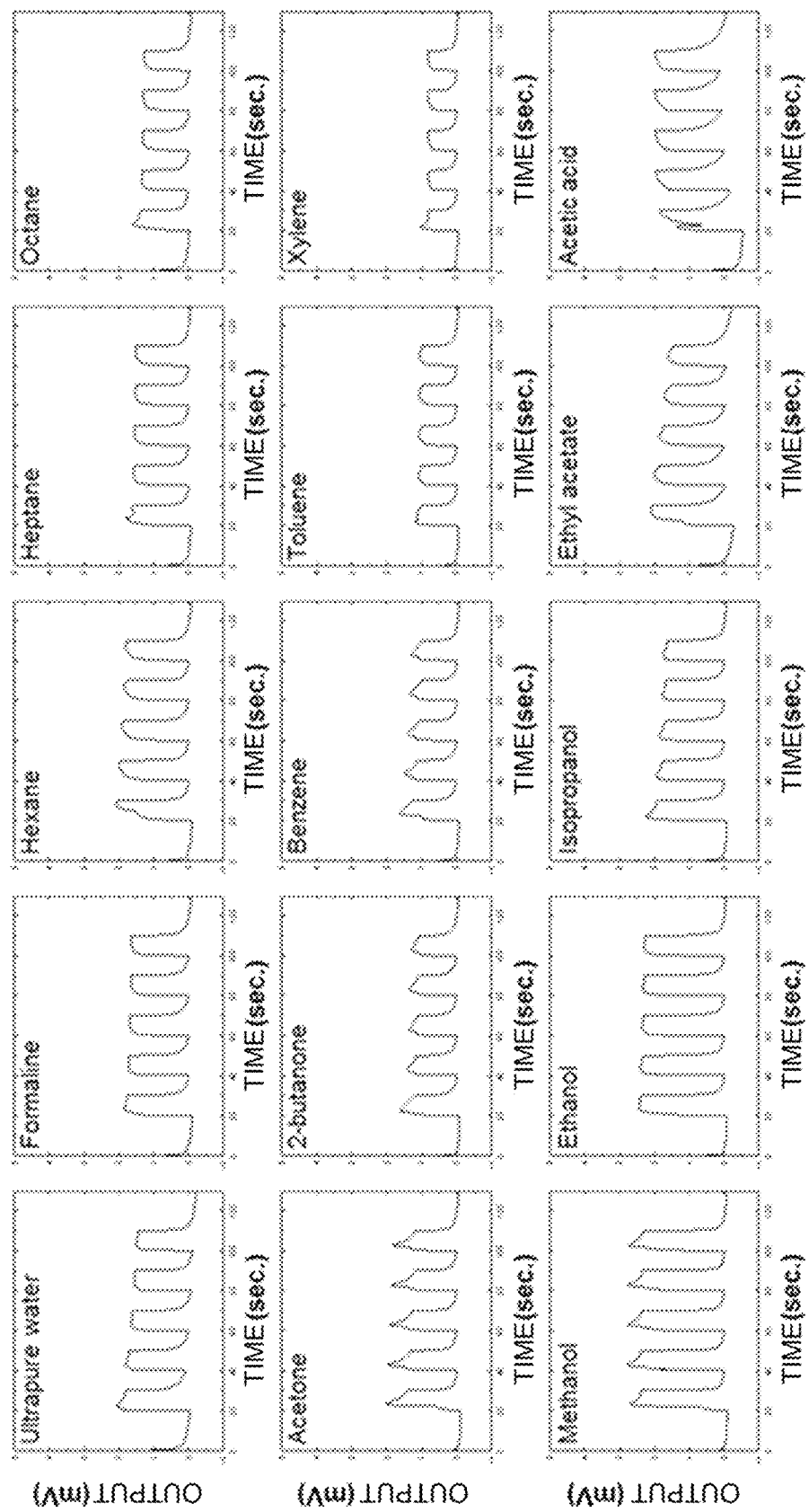
FIG. 11B is a diagram illustrating responses of Vinyl-STNPs-coated MSS to the 15 types of chemical substances. The names of the chemical substances are written at the top of each graph. The numerical values on the horizontal axis of each graph are 0, 20, 40, 60, 80, 100, and 120 while the numerical values on the vertical axis are −1, 0, 1, 2, 3, 4, and 5.
Figure 11C:
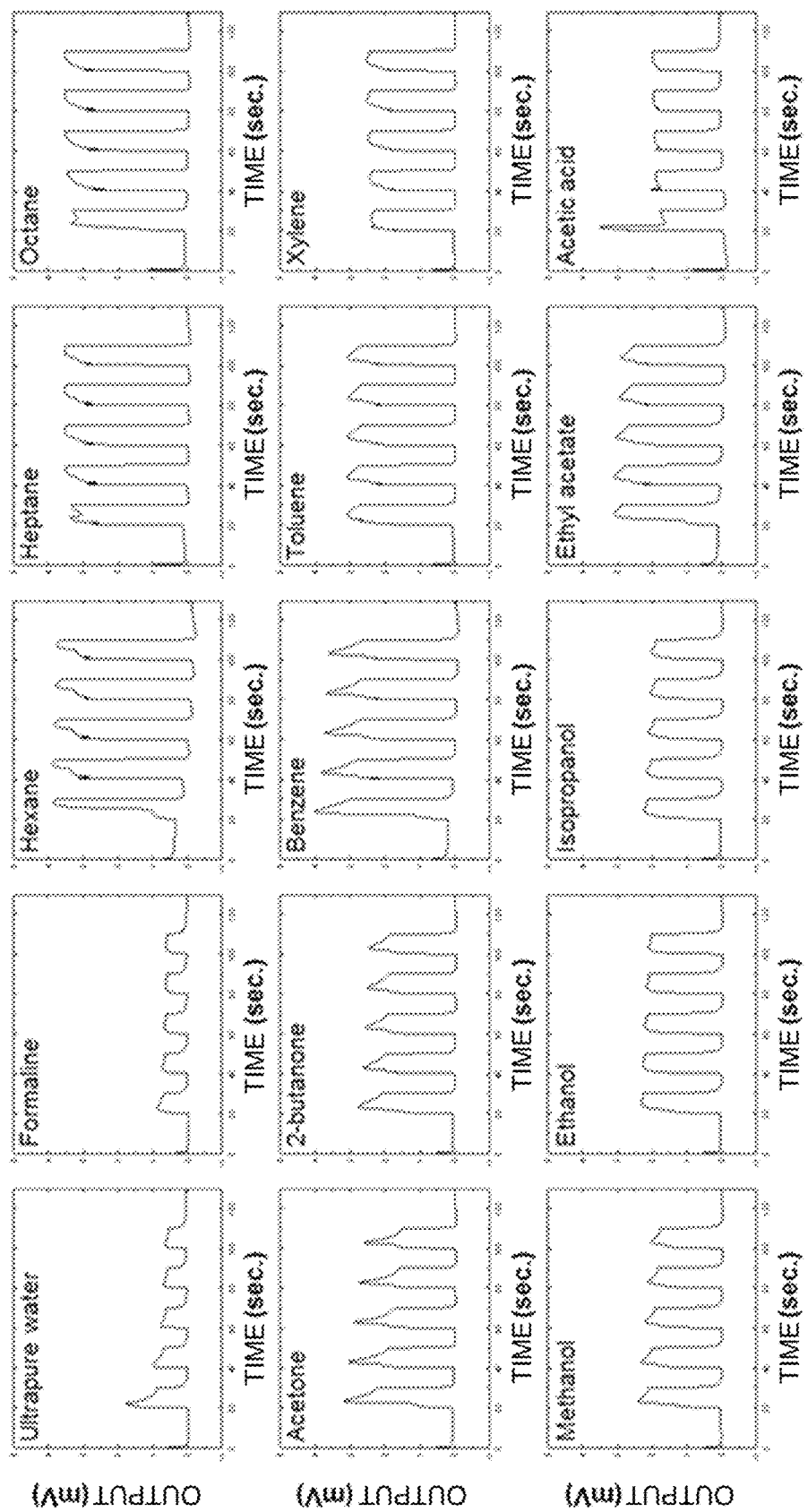
FIG. 11C is a diagram illustrating responses of C18-STNPs-coated MSS to the 15 types of chemical substances. The names of the chemical substances are written at the top of each graph. The numerical values on the horizontal axis of each graph are 0, 20, 40, 60, 80, 100, and 120 while the numerical values on the vertical axis are −1, 0, 1, 2, 3, 4, and 5.
Figure 11D:
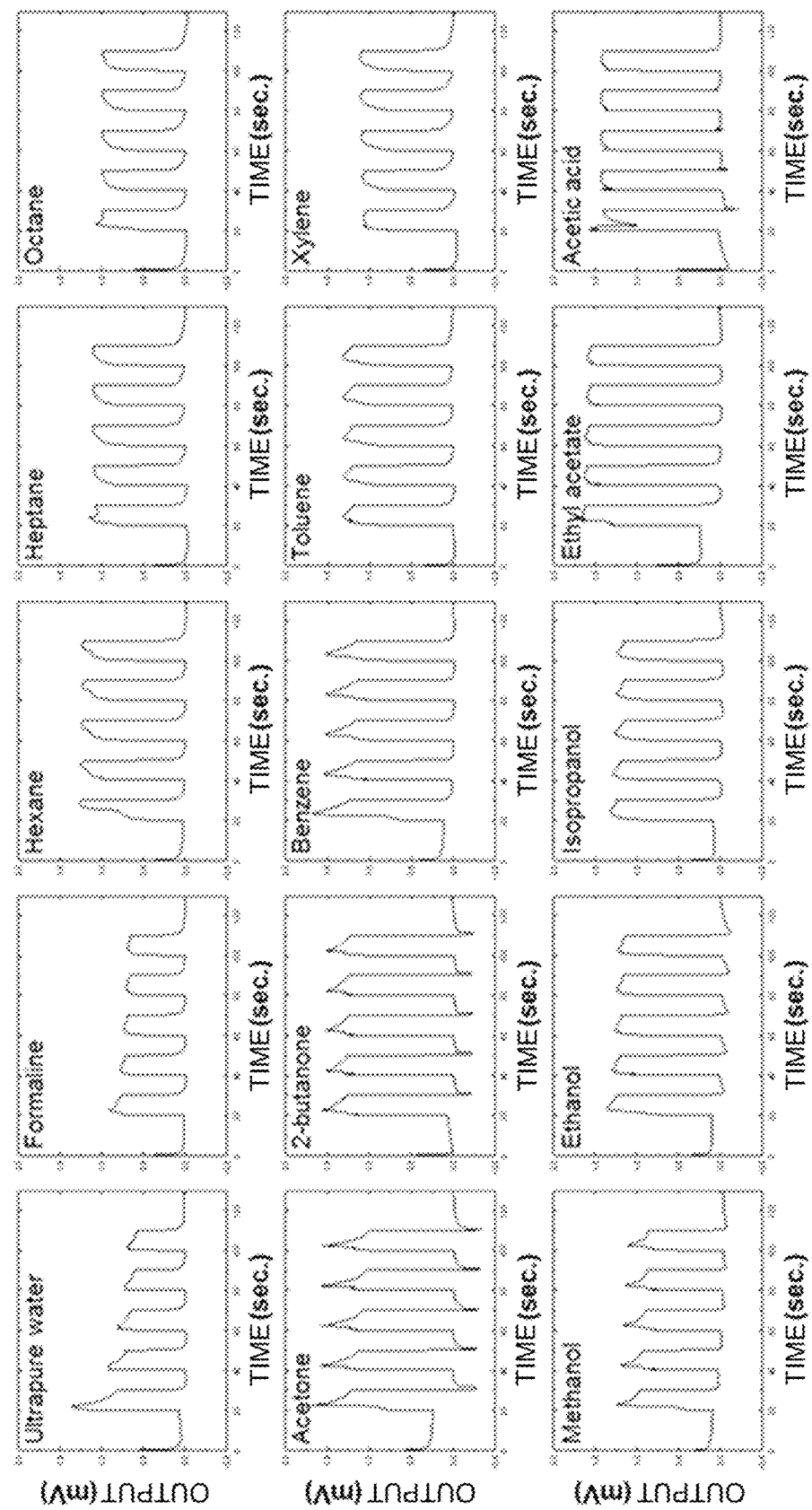
FIG. 11D is a diagram illustrating responses of Phenyl-STNPs-coated MSS to the 15 types of chemical substances. The names of the chemical substances are written at the top of each graph. The numerical values on the horizontal axis of each graph are 0, 20, 40, 60, 80, 100, and 120 while the numerical values on the vertical axis are −0.5, 0, 0.5, 1.0, 1.5, and 2.0.
Figure 12A:
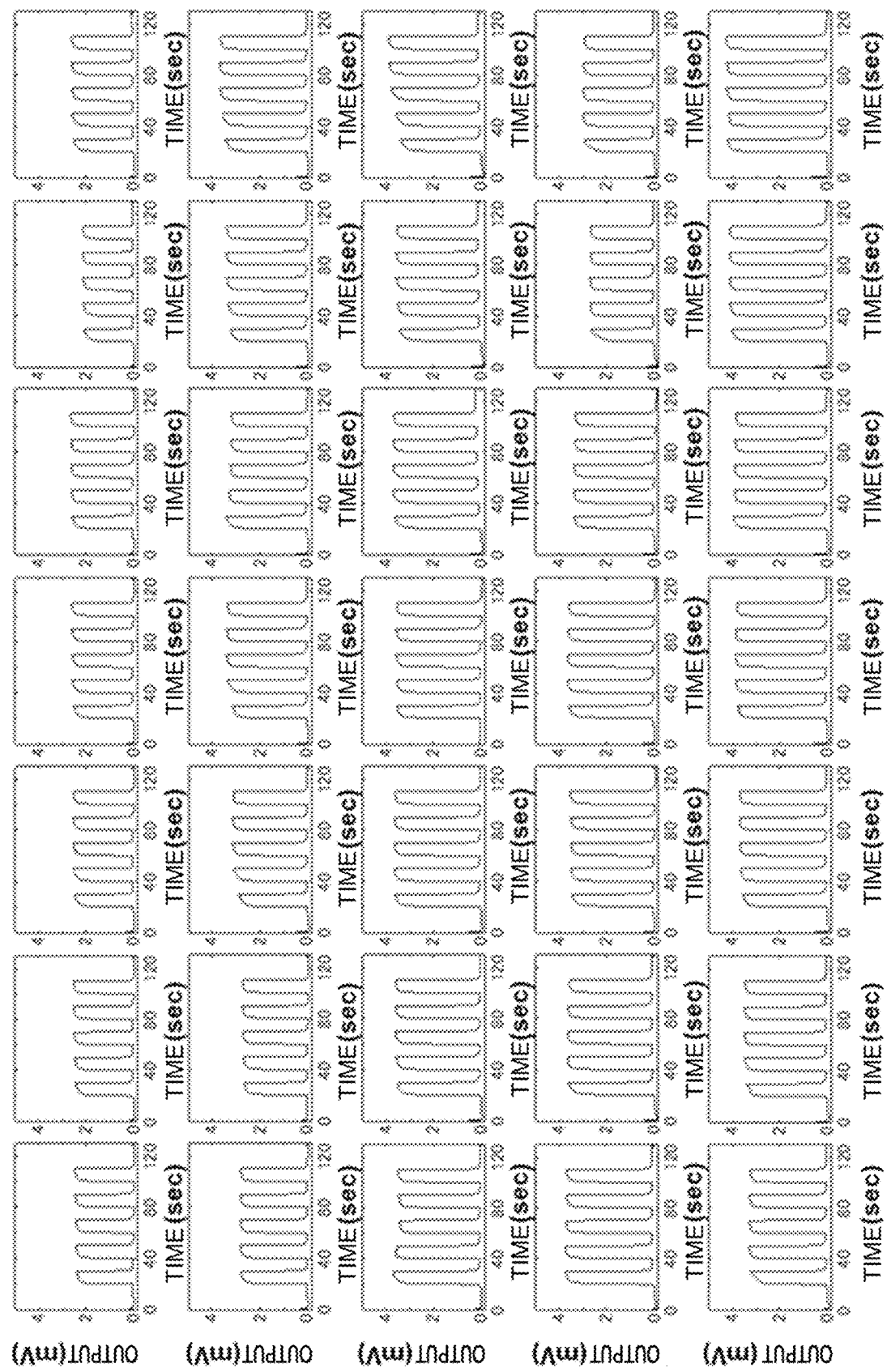
FIG. 12A is a diagram illustrating responses of Aminopropyl-STNPs-coated MSS to the 35 types of liquid specimens, including water, tea, EtOH aqueous solution, and alcoholic beverages of various compositions.
Figure 12B:
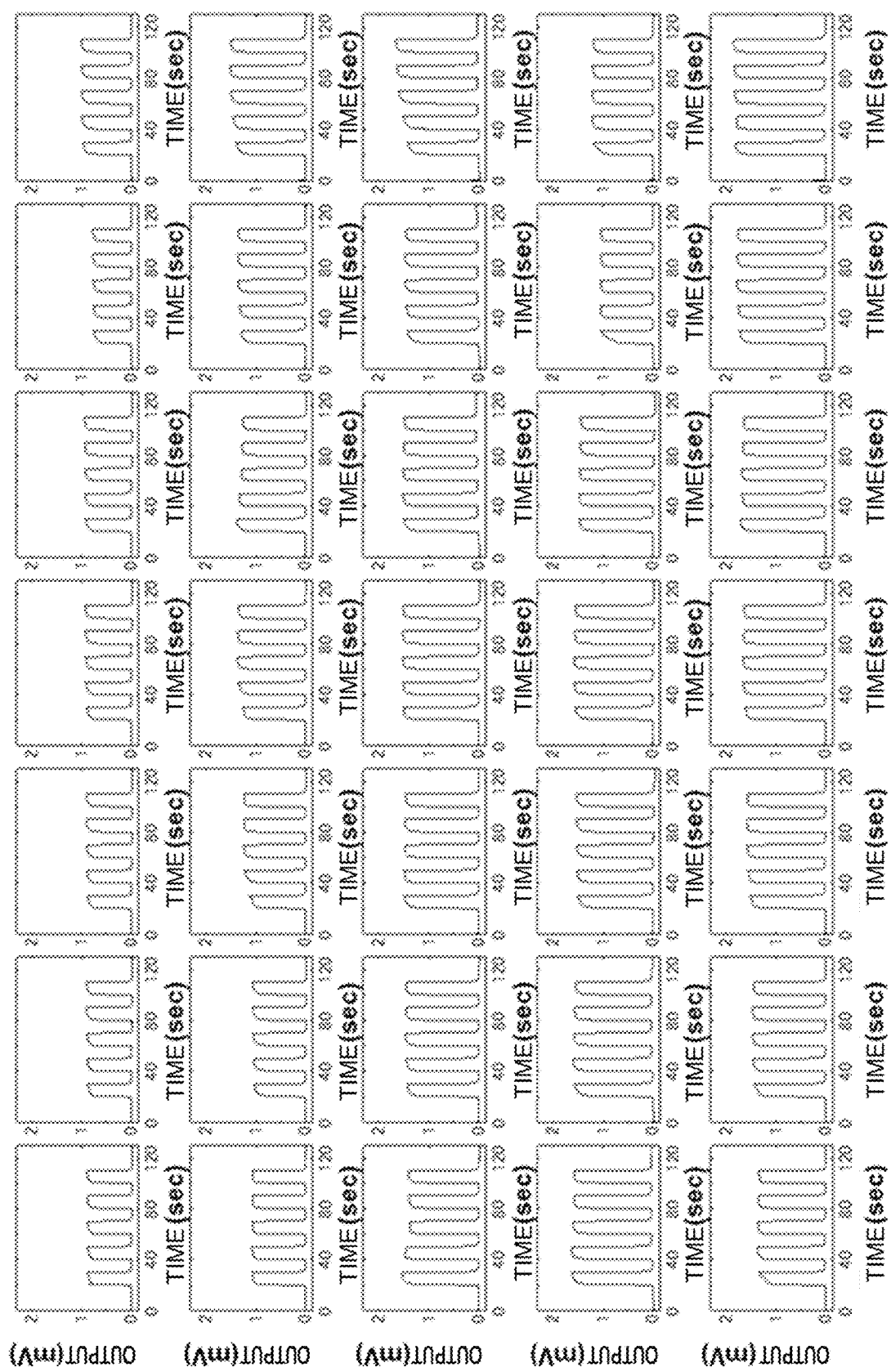
FIG. 12B is a diagram illustrating responses of Vinyl-STNPs-coated MSS to the 35 types of liquid specimens, including water, tea, EtOH aqueous solution, and alcoholic beverages of various compositions.
Figure 12C:
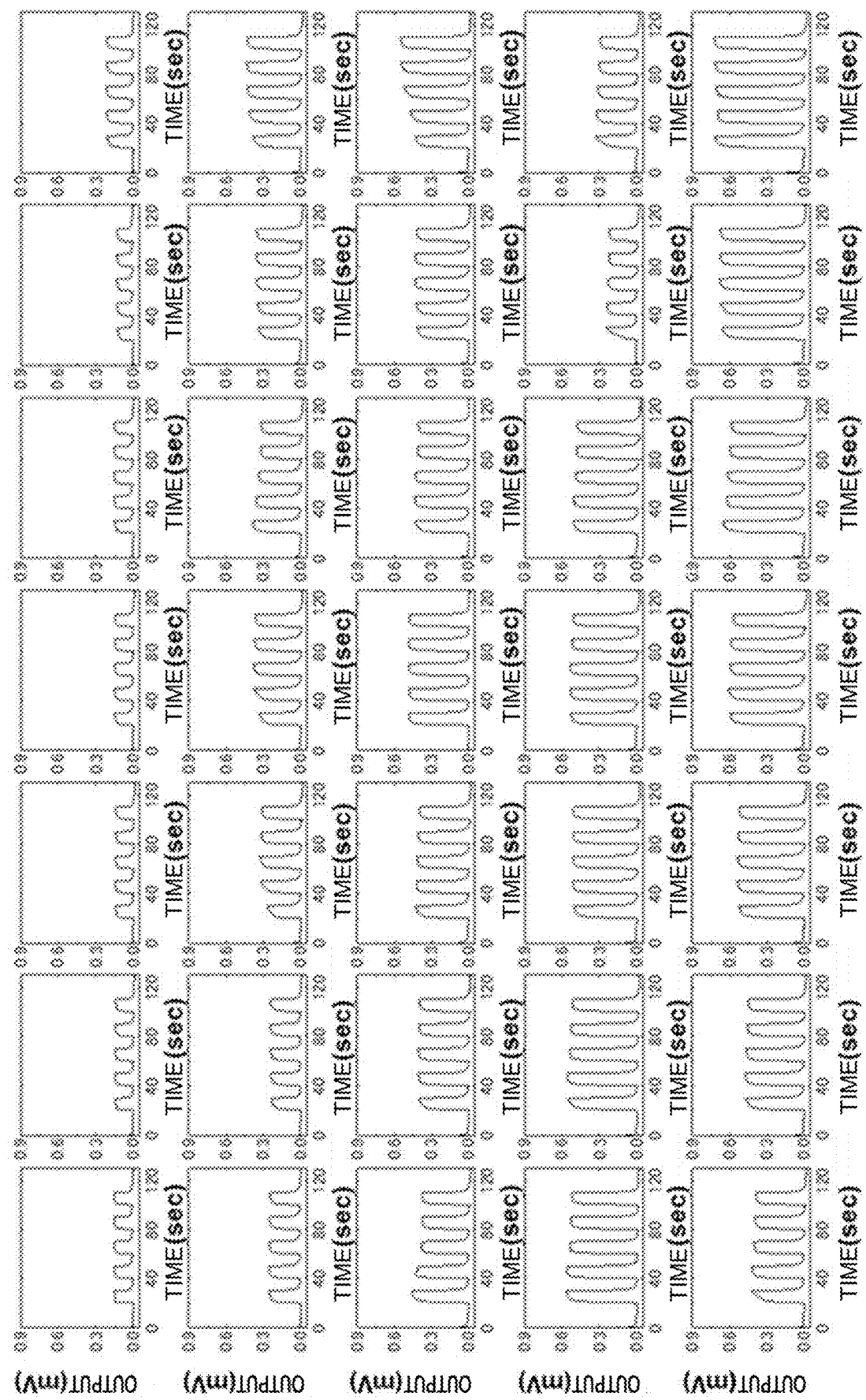
FIG. 12C is a diagram illustrating responses of C18-STNPs-coated MSS to the 35 types of liquid specimens, including water, tea, EtOH aqueous solution, and alcoholic beverages of various compositions.
Figure 12D:
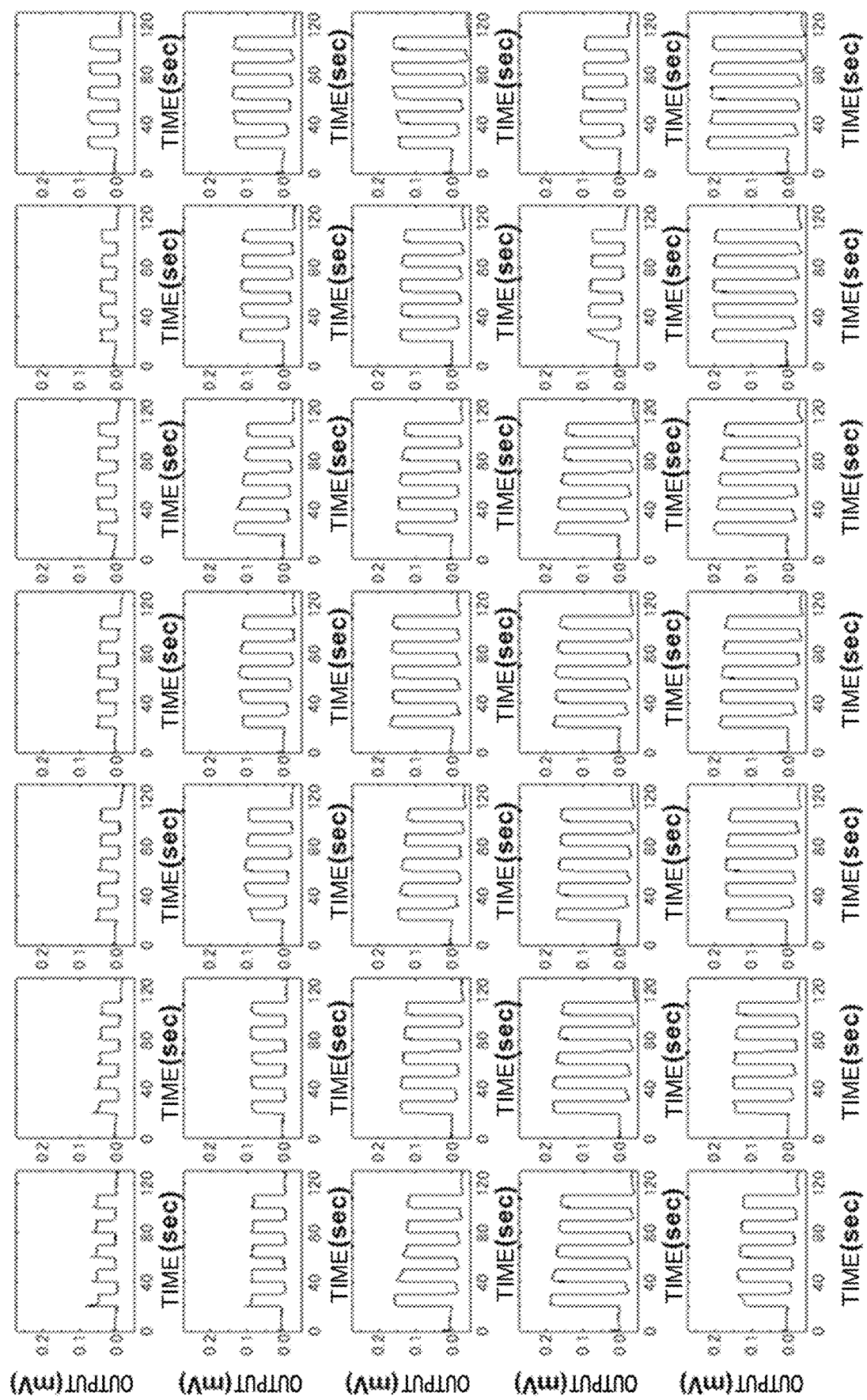
FIG. 12D is a diagram illustrating responses of Phenyl-STNPs-coated MSS to the 35 types of liquid specimens, including water, tea, EtOH aqueous solution, and alcoholic beverages of various compositions.
Figure 13A:
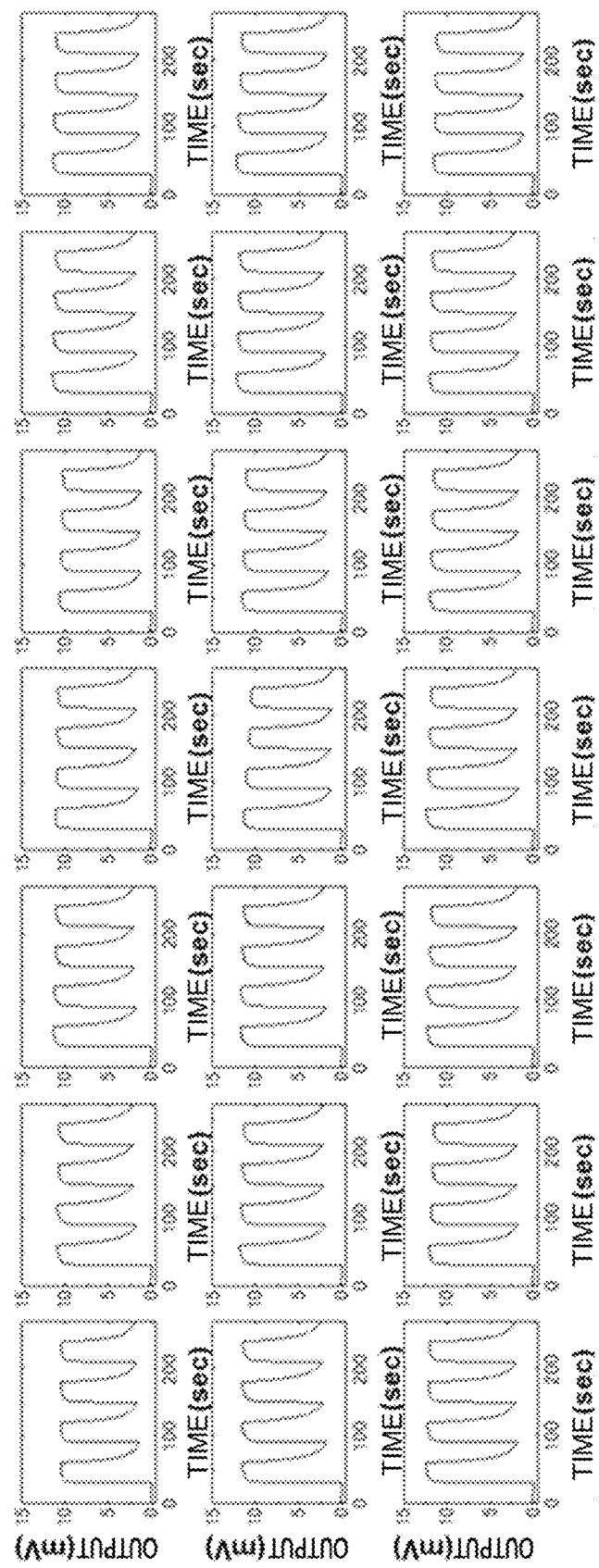
FIG. 13A is a diagram illustrating responses in a $N_2$ environment, of Aminopropyl-STNPs-coated MSS to the 21 types of liquid specimens, including water, EtOH aqueous solution, and alcoholic beverages.
Figure 13B:
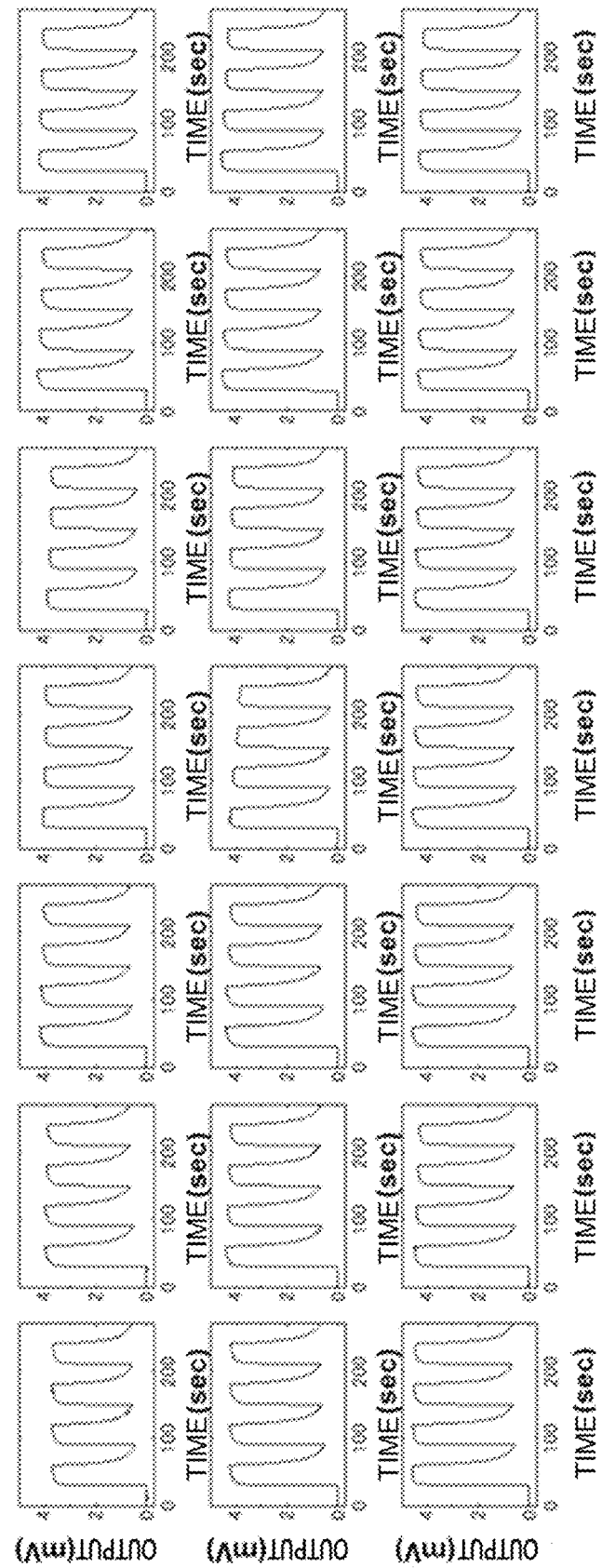
FIG. 13B is a diagram illustrating responses in a $N_2$ environment, of Vinyl-STNPs-coated MSS to the 21 types of liquid specimens, including water, EtOH aqueous solution, and alcoholic beverages.
Figure 13C:
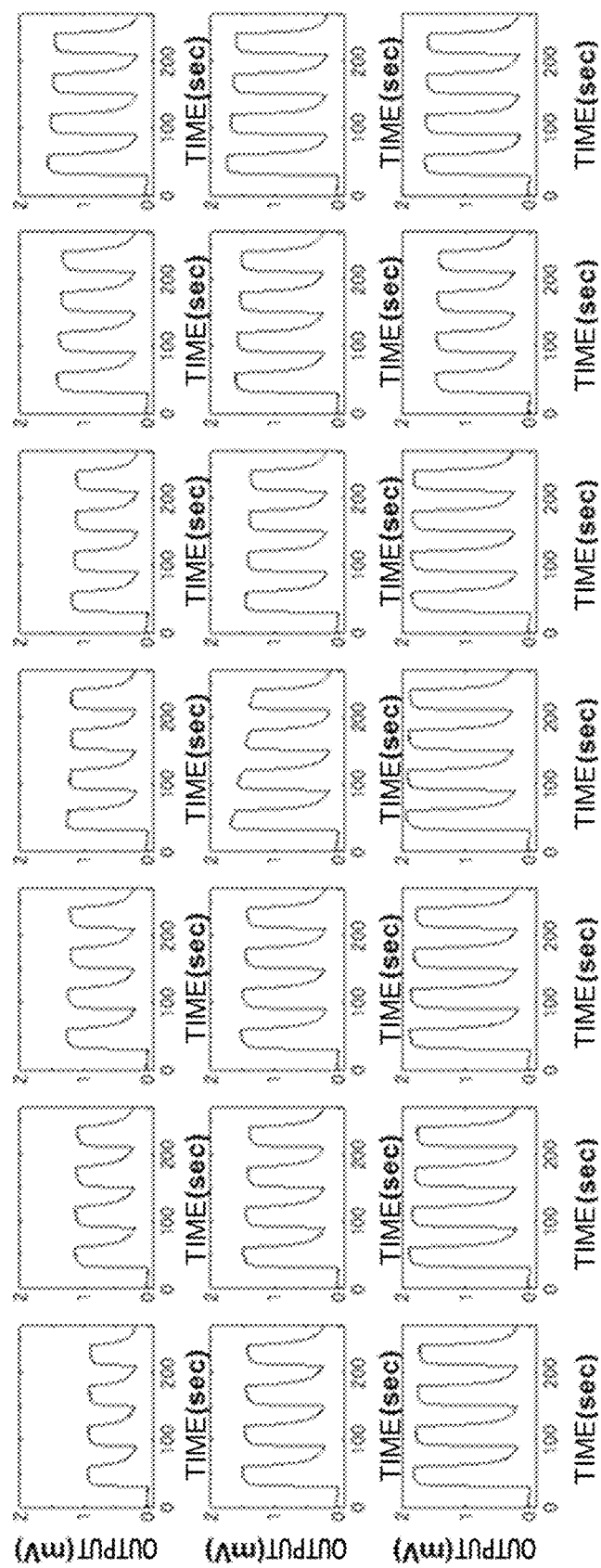
FIG. 13C is a diagram illustrating responses in a $N_2$ environment, of C18-STNPs-coated MSS to the 21 types of liquid specimens, including water, EtOH aqueous solution, and alcoholic beverages.
Figure 13D:
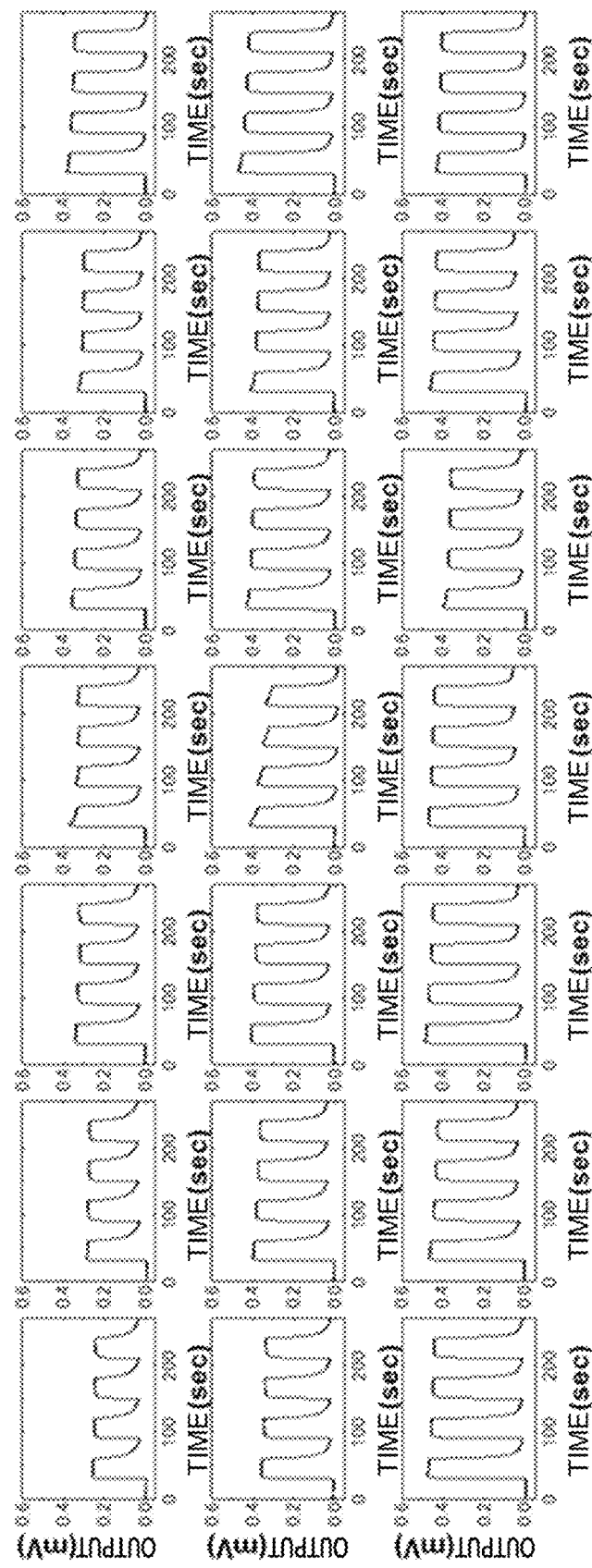
FIG. 13D is a diagram illustrating responses in a $N_2$ environment, of Phenyl-STNPs-coated MSS to the 21 types of liquid specimens, including water, EtOH aqueous solution, and alcoholic beverages.

To examine the performance of each of the four types of functionalized nanoparticles as the material of the receptor layer for nanomechanical sensing, the surface of MSS was coated with these nanoparticles by spray coating (described in detail later). As confirmed in each optical microscopic image illustrated in FIG. 10, the whole sensor surface was coated with the coating layer. The thickness of the coating was estimated to be approximately 1 μm. C18-STNPs and Phenyl-STNPs were not well dispersed in the mixture of water and IPA, and many aggregates are recognized in the optical microscopic images in FIG. 10.

The detection performance of each nanoparticle-coated MSS in an atmospheric environment was examined by performing measurements for 15 types of chemical substances. The sensor array used herein was composed of four MSS. The MSS in the sensor array are sometimes referred to as channels. These chemical substances are roughly classified into following six categories: water-based substances (ultrapure water and formalin (denoted by Ultrapure water (or Water) and Formaline in the drawings, respectively), alkanes (hexane, heptane, and octane (denoted by Hexane, Heptane, and Octane in the drawings, respectively)), alcohols (methanol, ethanol, and isopropanol (denoted by Methanol (or MeOH), Ethanol (or EtOH), and Isopropanol (or IPA), respectively), aromatic compounds (benzene, toluene, and xylene (denoted by Benzene, Toluene, and Xylene in the drawing, respectively), ketones (acetone and 2-butanone) (denoted by Acetone and 2-butanone in the drawing, respectively), and others (ethyl acetate and acetic acid (denoted by Ethyl acetate (or AcOEt) and Acetic acid in the drawing, respectively)). As apparent from response waveforms illustrated in FIGS. 11A to 11D, the four channels differently respond to those chemical substances. The trend of the response signals can be interpreted based on expected properties of nanoparticles used in each channel. For example, Aminopropyl-STNPs and Phenyl-STNPs well responded to the water-based substances and alcohols while C18-STNPs and Phenyl-STNPs well responded to aromatic compounds. C18-STNPs especially exhibited the highest affinity with alkanes as expected from the structural similarity.

Figure 3:
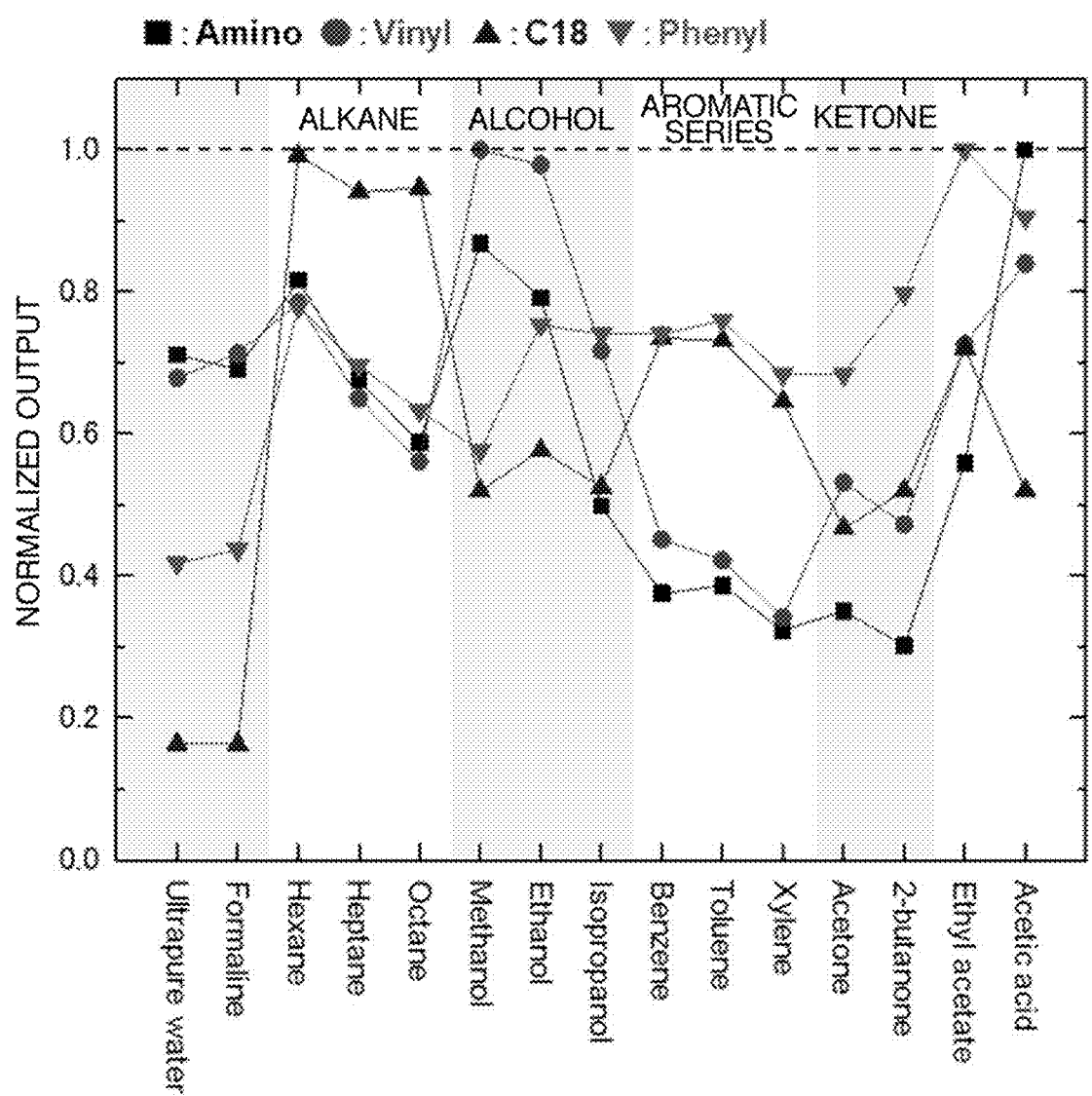
FIG. 3 is a diagram illustrating the affinity trend of the four types of nanoparticles used in Examples of the invention. In the diagram, normalized outputs are defined based on the signal intensity of the third response cycle in FIGS. 11A to 11D. The first and second responses are omitted because an elapse of a certain period of time is necessary to obtain stable reproducible responses.
Figure 4:
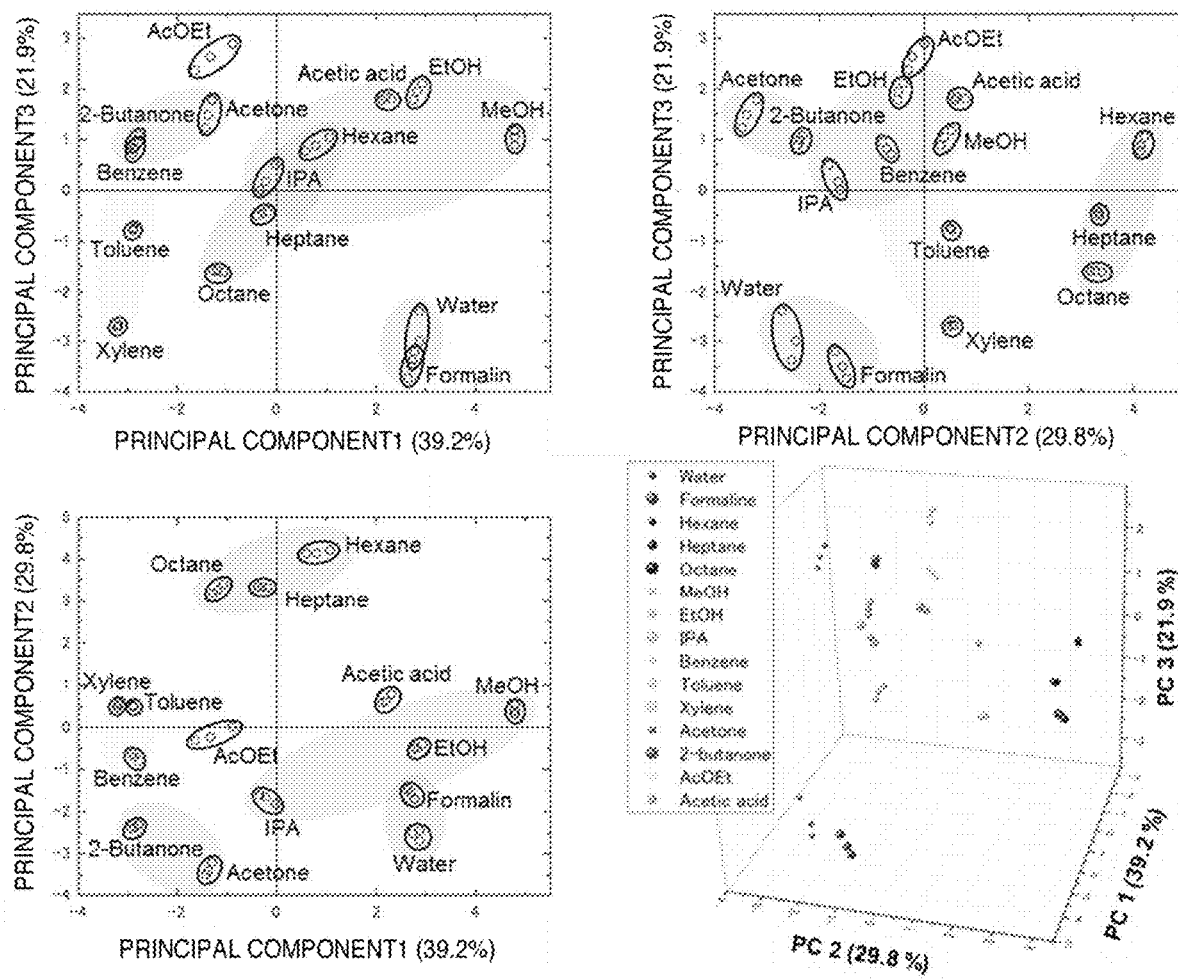
FIG. 4 is a diagram illustrating principal component analysis (PCA) plots to identify 15 types of chemical substances using nanoparticle-coated MSS.

As illustrated in FIG. 3, these channels complement each other to provide a good response property to the various types of chemical substances. The combination of the aforementioned functionalized nanoparticles used as the receptor layer material for detection therefore can provide adequate identification ability. To verify this idea, principal component analyses (PCA) were performed for data sets obtained as a result of measuring these 15 types of chemical substances. The PCA plots illustrated in FIG. 4 represent that these chemical substances can be clearly identified in accordance with the chemical structures thereof (Estimation of Alcohol Concentration of Various Alcoholic Beverages Based on Machine Learning)

As described above, the sensor array including various functionalized channels was able to identify a lot of chemical substances by just extracting simple parameters from the measured response signals (described in detail later with reference to FIG. 6). This means that such a sensor array including multiple channels that exhibit different responses to each of multiple types of chemical substances described above has the potential to be a good means to extract quantitative information from a specimen of a complicated composition, such as odor. In Examples, odor of various alcoholic beverages, that is, vapor generated from the same was used as a model example of machine learning (ML). To be specific, a lot of training data concerning odor of alcoholic beverages were collected for machine learning. Based on the machine learning, the alcohol concentration of an unknown alcoholic beverage was estimated.

Figure 5:
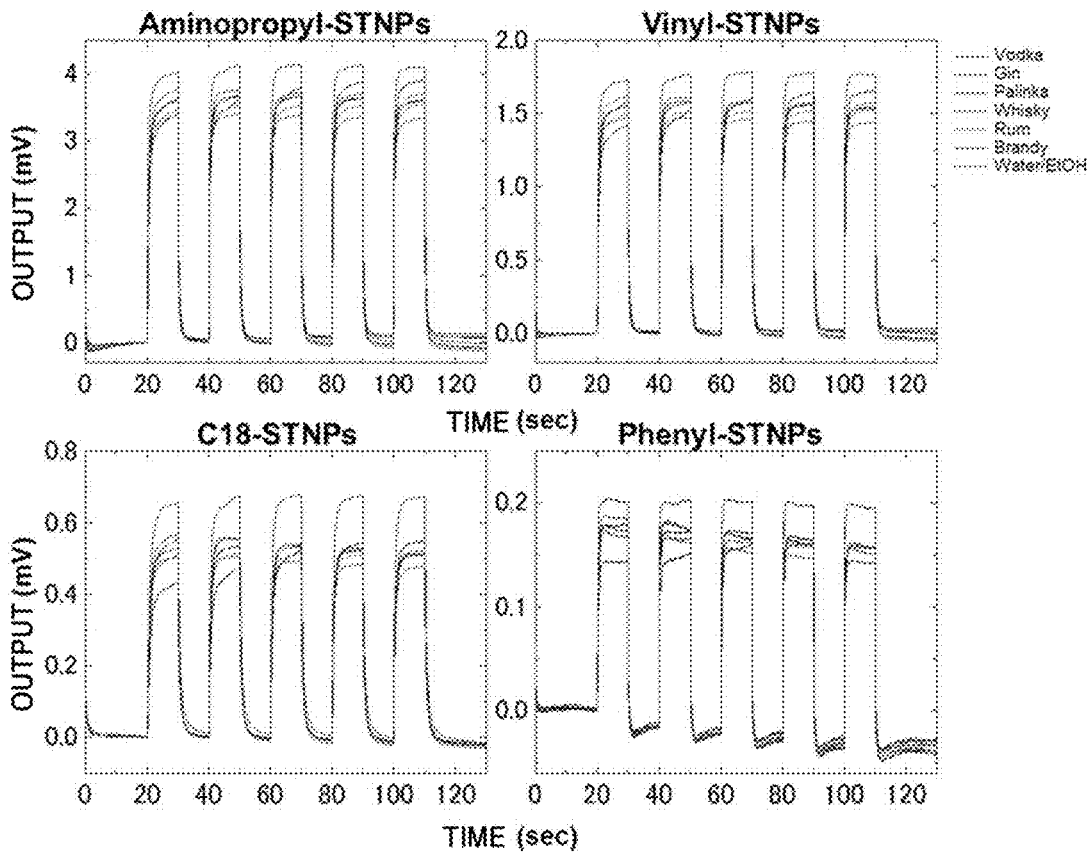
FIG. 5 is a diagram illustrating signals measured from seven types of alcoholic beverages with the same alcohol concentration (40%). Even in measurement using the same receptor coating, different types of alcoholic beverages produce different response waveforms/intensities.

First, odor of the 35 types of liquid specimens was measured, and responses to the odor from the sensor array that includes channels coated with the aforementioned four types of nanoparticles were obtained. As illustrated in FIGS. 12A to 12D, it was confirmed that those responses were different from each other in terms of the shape and intensity. The 35 types of liquid specimens were commercially available alcoholic beverages, non-alcoholic beverages, and just mixtures of water and ethyl alcohol (EtOH). As illustrated in FIG. 5, for example, even the liquid specimens of the same alcohol concentration (40%) provide different response waveforms. These results have revealed that it is nearly impossible to calculate the alcohol concentration directly from the measurement signals. Furthermore, it is reported that when the system to be measured includes three or more components, it is practically difficult to determine the content of each component (Non-patent Literature 3). Accordingly, instead of analytic calculation for the content of a specific component from the response signal, the correlation between response signals concerning the alcohol concentration was learned by using a machine learning technique. Thus, the machine learning model for estimating the alcohol concentration of an alcoholic beverage from a signal measured by the sensor array was constructed.

As the machine learning technique, various techniques are available, and kernel ridge regression (KRR) was employed in Examples by way of example. Hyperparameters of KRR were determined so as to minimize prediction error Δ (denoted by Prediction error in the drawing; described in detail later) which was obtained by cross validation. KRR and cross validation are described in detail later. To perform KRR, features of a signal measured by each channel of the sensor array are represented by parameters (parameters 1 to 4, denoted by Parameters 1 to 4 in the drawing) defined as follows.

[MATH. 1]

Parameter 1: $(b-a)/(t_b-t_a)$   (1)

Parameter 2: $(c-b)/(t_c-t_b)$   (2)

Parameter 3: $(d-c)/(t_d-t_c)$   (3)

Parameter 4: $(e-a)$   (4)

Figure 6:
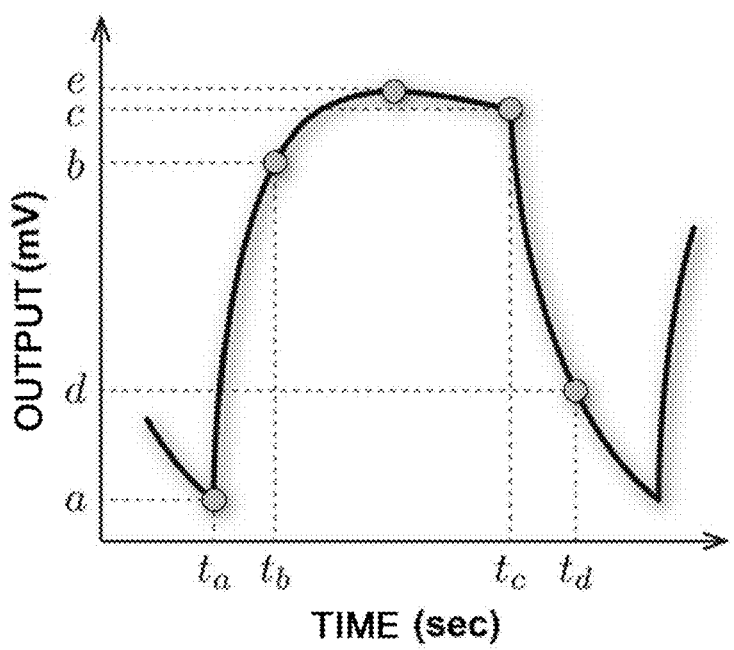
FIG. 6 is a diagram schematically explaining feature extraction from signals measured by MSS. Four parameters are defined as features using measured signal values a, b, c, d, and e and normalized times $t_a$, $t_b$, $t_c$, and to corresponding to those values.

Herein, a, b, c, d, and e are signal values extracted as illustrated in FIG. 6 from each cycle of the response signal from each channel when odor (vapor) and reference gas (air or $N_2$) were supplied to a sensor array while alternating with each other in a predetermined cycle. $t_a$, $t_b$, $t_c$, and $t_d$ are the times corresponding to the same. More specifically, $t_b=t_a+1$ (sec), $t_c=t_a+10$ (sec), and $t_d=t_a+11$ (sec) herein. Each signal includes multiple peaks, and ta of each peak has a different value. The physical meaning of Parameter 1 relates to an adsorption process of a substance to be measured while Parameter 3 includes information concerning a desorption process. Parameter 2 is defined as an inclination between the adsorption and desorption processes, which is regarded as a quasi-equilibrium state where adsorption is becoming static. This cannot be called equilibrium for some combinations of the receptor and specimen molecules. In associating adsorption Parameter 3 with desorption, gradual changes in Parameters 1 and 3 are defined as quasi-equilibrium. Parameter 4 is defined as the maximum height obtained from the curve in each cycle of the response signal. This reflects the adsorption capacity of the receptor layer.

Figure 7:
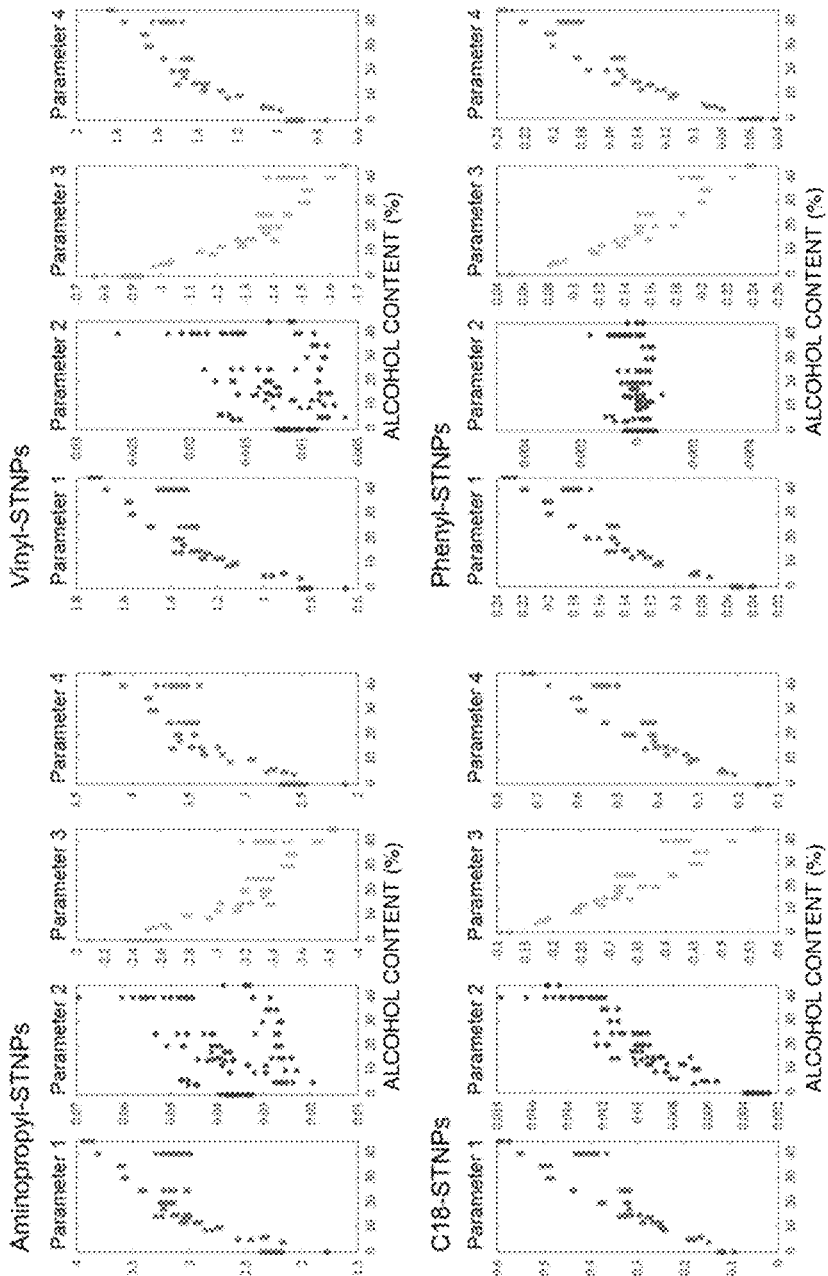
FIG. 7 is a diagram illustrating alcohol concentration dependence of parameters extracted from signals measured in an atmospheric environment.

FIG. 7 illustrates the alcohol concentration dependence of the parameters extracted from signals of the 35 types of alcoholic beverages measured by the sensor array using the aforementioned four types of nanoparticles (the measurement method is described in detail later). The specific names of the 35 types of alcoholic beverages are described later. It should be noted that the "alcoholic beverages" herein also include liquid, such as tap water not containing alcohol, and liquid which contains alcohol but is usually not regarded as an alcoholic beverage (specifically, alcohol just diluted with water).

For each alcoholic beverage, three peaks at $t_a=60$, 80, and 100 were used. Each graph of FIG. 7 includes 105 data points. It was confirmed that the parameters, except for Parameter 2, had a certain degree of correlation with the alcohol concentration. This means that Parameters 1, 3, and 4 are useful to train the machine learning model for the alcohol concentration. On the other hand, at this stage, it cannot be concluded which receptor layer material is suitable for estimating the alcohol concentration.

Figure 8:
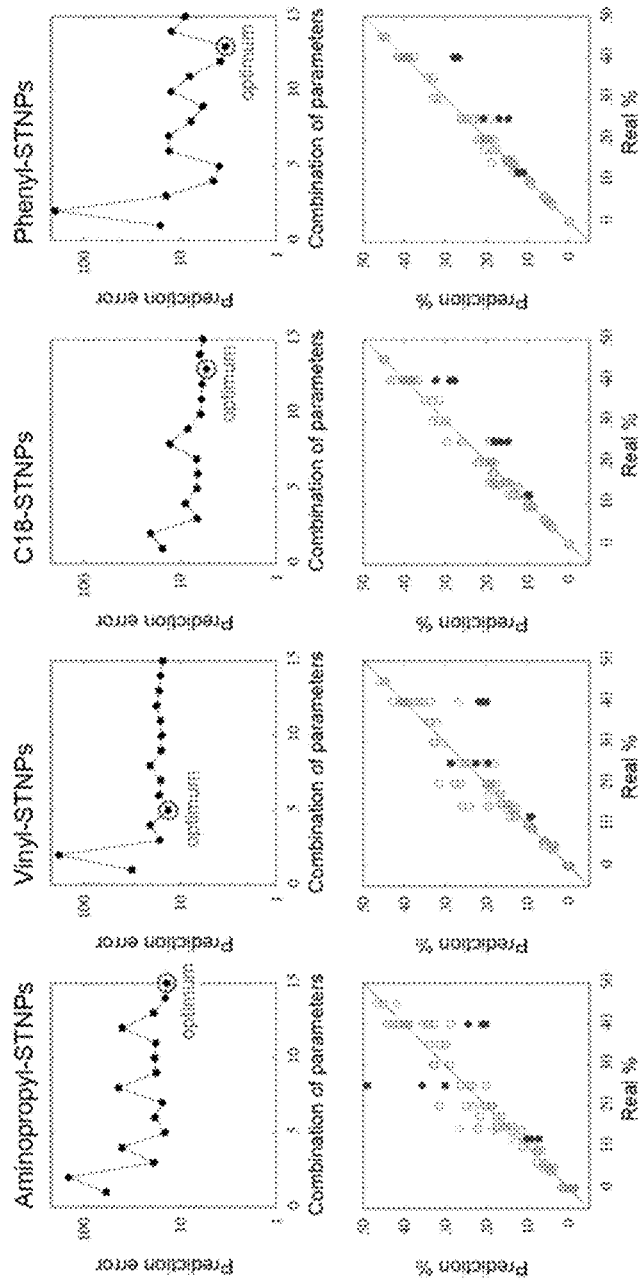
In FIG. 8, upper diagrams illustrate dependence of prediction error on the combination of four parameters extracted from signals measured in an atmospheric environment. Numerical values indicating combinations of parameters (denoted by combination of parameters on the horizontal axis in each graph) are represented by decimals of 1 to 15. Each bit digit of a numerical value represented in a 4-bit binary number indicates whether the corresponding parameter is used in the combination of interest. When the first digit of the binary number is 0, parameter 1 is not used, and otherwise, parameter 1 is used. Similarly, the second to fourth digits of the binary number indicate whether parameters 2 to 4 are used, respectively. The case is not considered where none of parameters 1 to 4 is used, and the numerical value indicating the combination of parameters does not take 0. When the numerical value indicating the combination of parameters is 10, which is 1010 in binary notation, parameters 2 and 4 are used in this combination.

Those extracted parameters were used to perform KRR. For all the combinations of the four parameters for each receptor layer material, machine learning models were trained to predict the alcohol concentration of alcoholic beverages ("to predict" means "to estimate" in this application). The number of the trained machine learning models was $2^4-1$, that is, 15. 32 types of alcoholic beverages, out of the 35 types of alcoholic beverages (other than red wine, sweet potato shochu, and whiskey), were used for training as known data. The training of machine learning models uses three signals at $t_a=60$, 80, and 100 for each alcoholic beverage, totally 96 (=3×32) signals. The four graphs on the upper side in FIG. 8 illustrate the prediction error Δ that depends on the combination of parameters when 24-fold cross-validation was performed. The optimal value of the prediction error and the optimal combination of parameters (denoted by optimum in each graph for each receptor layer material on the upper side of FIG. 8) for each receptor layer material are summarized in Table 1 below.

Table 1: Optimal Combination of Parameters and Optimal Prediction Error Depending on Receptor Layer Material Under Atmospheric Conditions

TABLE 1

|  | Aminopropyl | Vinyl | C18 | Phenyl |
|---|---|---|---|---|
| Parameter 1 | ✓ | ✓ | ✓ | ✓ |
| Parameter 2 | ✓ | — | — | — |
| Parameter 3 | ✓ | ✓ | ✓ | ✓ |
| Parameter 4 | ✓ | — | ✓ | ✓ |
| Prediction Error | 13.7373 | 13.2925 | 5.3103 | 3.3576 |

Table 1 suggests that C18-STNPs and Phenyl-STNPs are more useful than Aminopropyl-STNPs and Vinyl-STNPs to predict the alcohol concentration of alcoholic beverages. This result cannot be obtained by just extracting the parameters. In addition, it was confirmed that Parameter 2 is not useful to predict the alcohol concentration as expected.

Figure 14A:
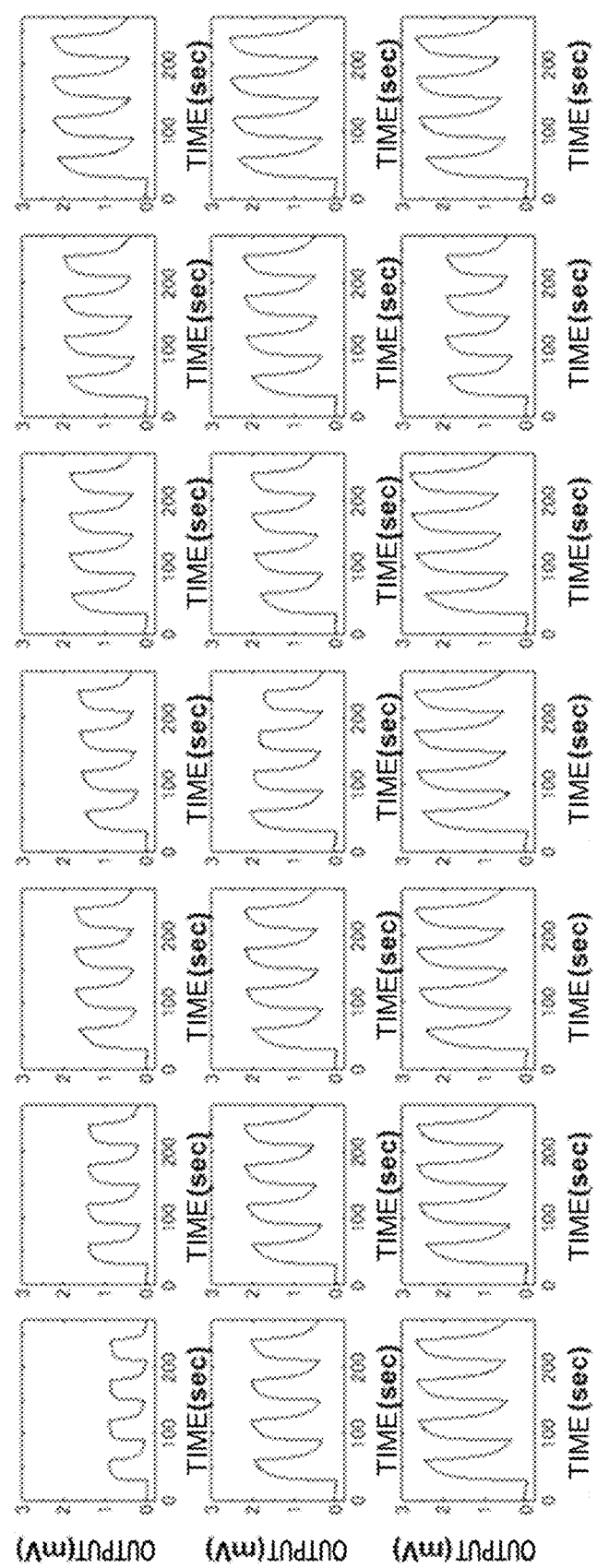
FIG. 14A is a diagram illustrating responses in a $N_2$ environment, of polysulfone-coated MSS to the 21 types of liquid specimens, including water, EtOH aqueous solution, and alcoholic beverages.
Figure 14B:
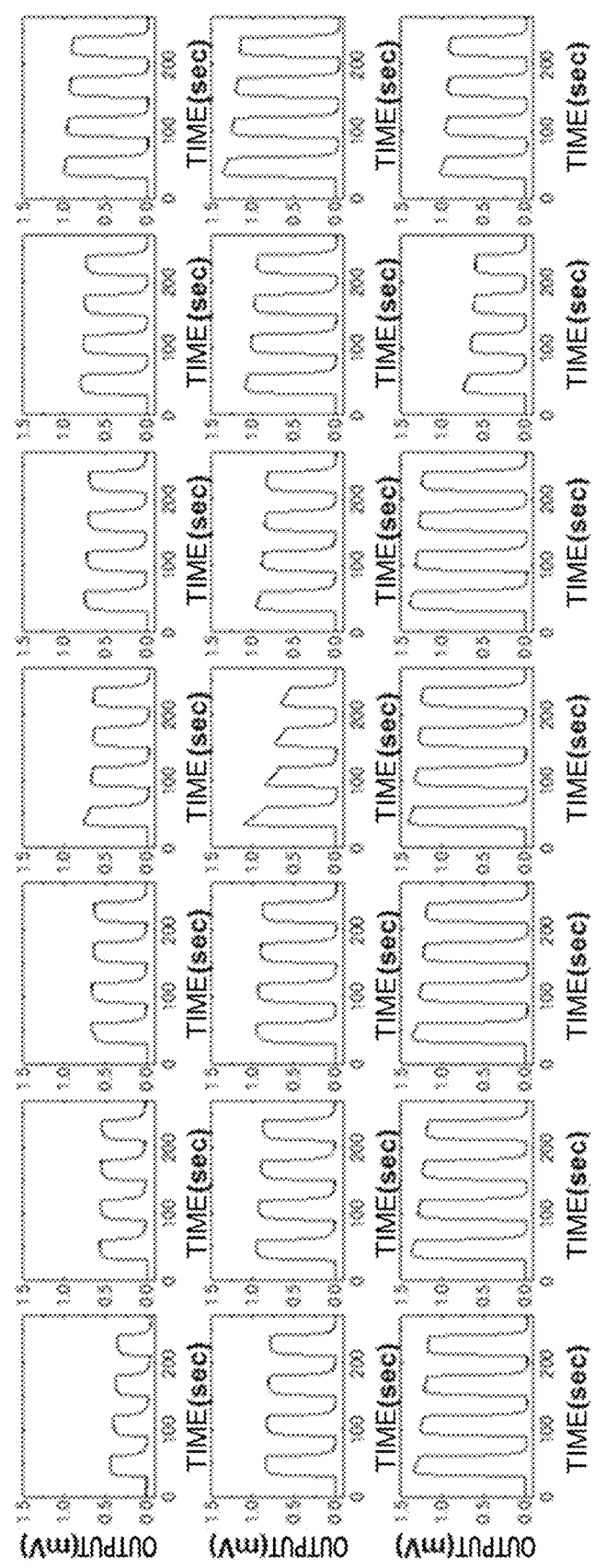
FIG. 14B is a diagram illustrating responses in a $N_2$ environment, of polycaprolactone-coated MSS to the 21 types of liquid specimens, including water, EtOH aqueous solution, and alcoholic beverages.
Figure 15A:
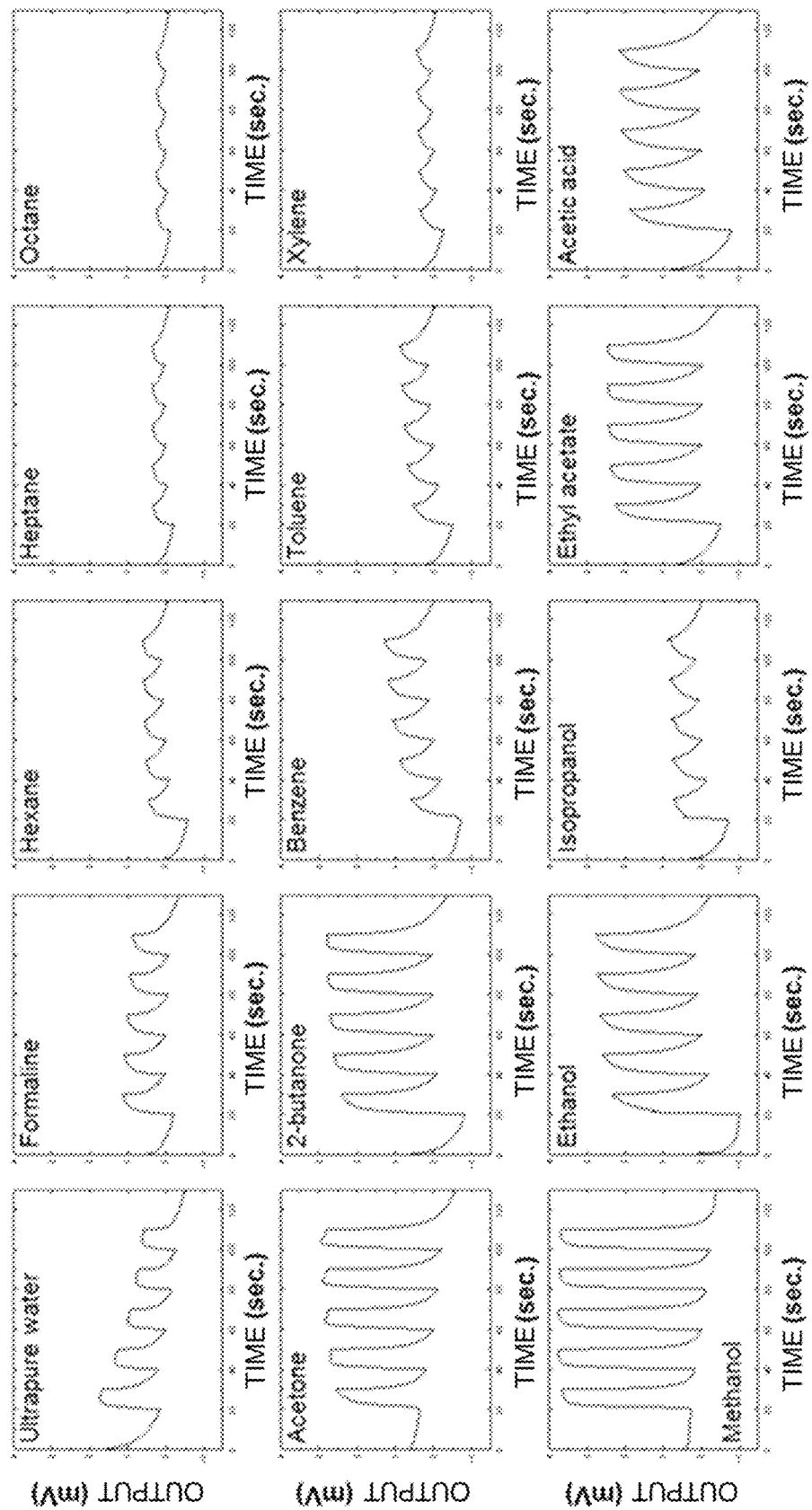
FIG. 15A is a diagram illustrating responses of polysulfone-coated MSS to the 15 types of chemical substances. The names of the chemical substances are written at the top of each graph. The numerical values on the horizontal axis of each graph are 0, 20, 40, 60, 80, 100, and 120 while the numerical values on the vertical axis are −1, 0, 1, 2, 3, and 4.
Figure 15B:
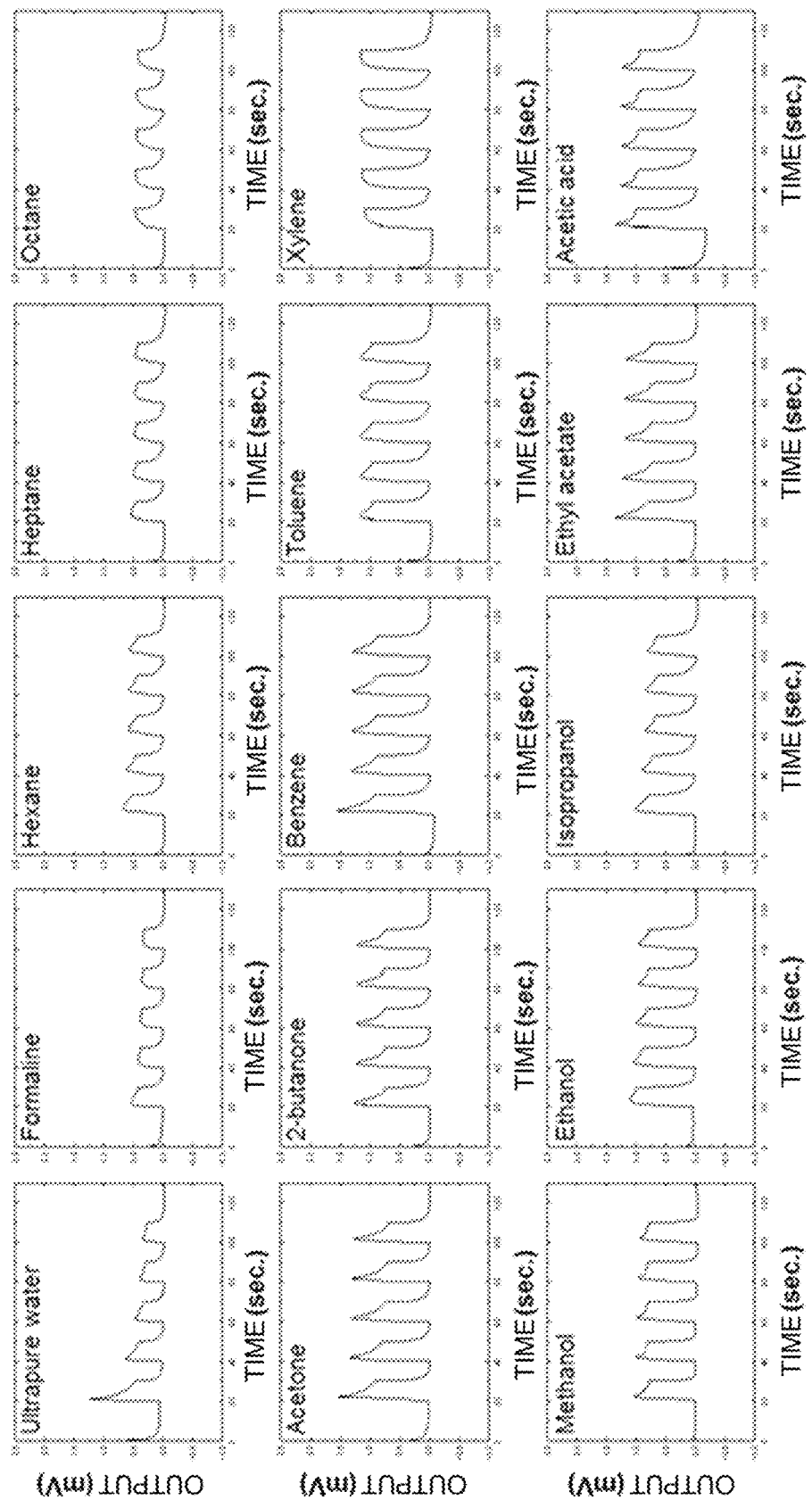
FIG. 15B is a diagram illustrating responses of polycaprolactone-coated MSS to the 15 types of chemical substances. The names of the chemical substances are written at the top of each graph. The numerical values on the horizontal axis of each graph are 0, 20, 40, 60, 80, 100, and 120 while the numerical values on the vertical axis are −1.0, −0.5, 0, 0.5, 1.0, 1.5, 2.0, and 2.5.
Figure 16A:
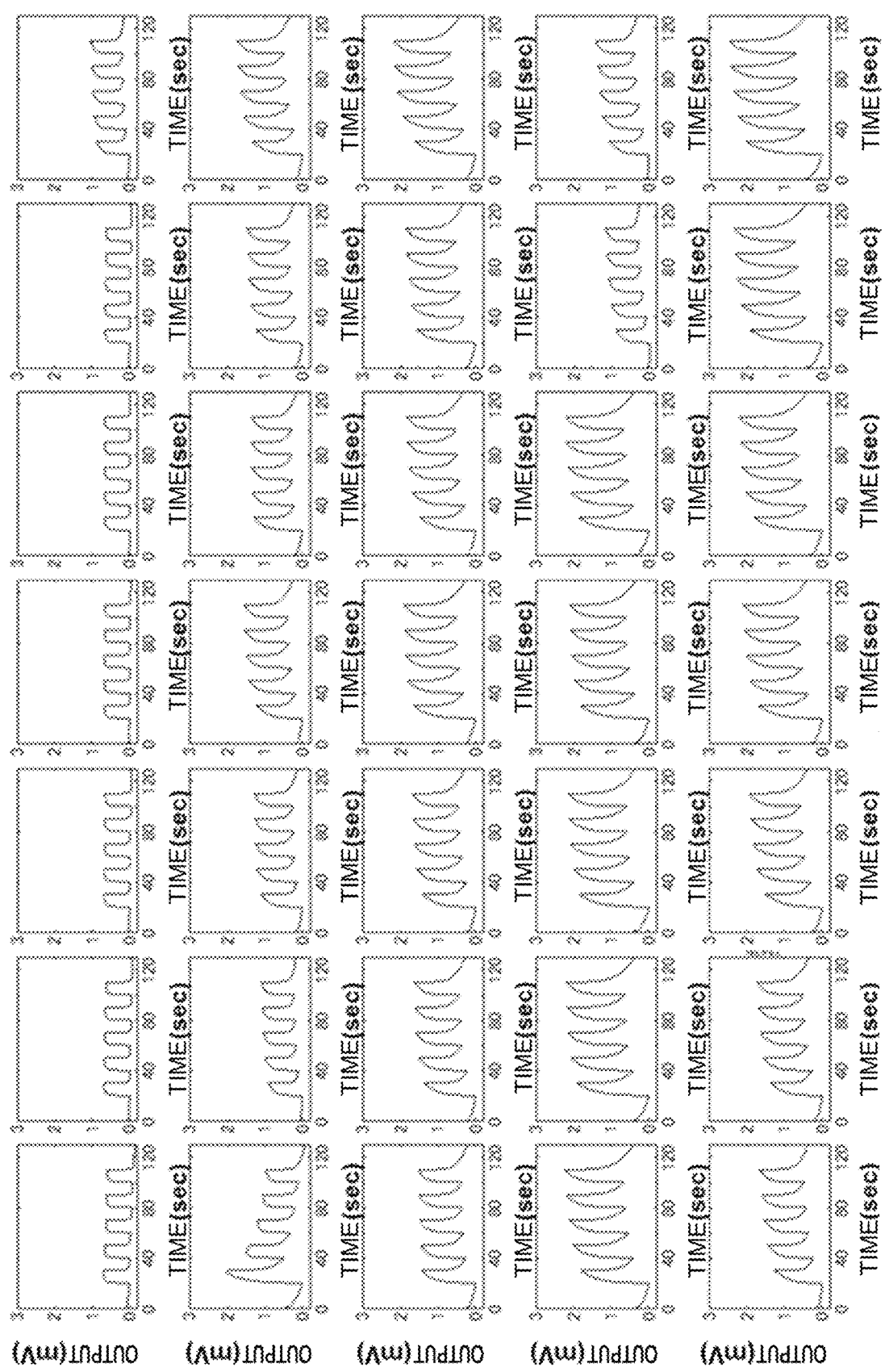
FIG. 16A is a diagram illustrating responses of polysulfone-coated MSS to the 35 types of liquid specimens, including water of various compositions, tea, EtOH aqueous solution, and alcoholic beverages.
Figure 16B:
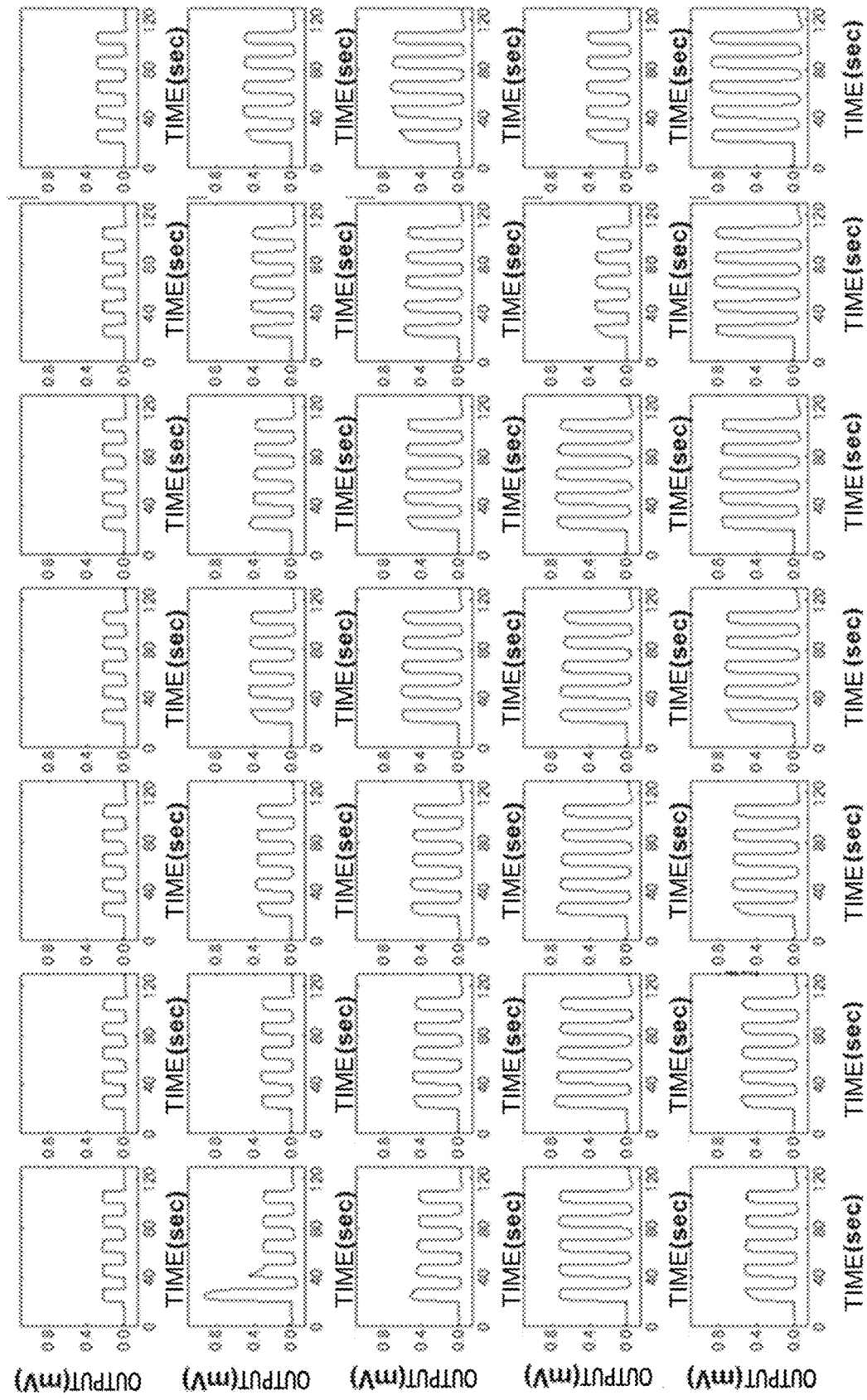
FIG. 16B is a diagram illustrating responses of polycaprolactone-coated MSS to the 35 types of liquid specimens, including water of various compositions, tea, EtOH aqueous solution, and alcoholic beverages.

Furthermore, parity plots of predicted alcohol concentration vs real alcohol concentration when the optimal combination of parameters was used are illustrated by the graphs in the lower side of FIG. 8. In these graphs, the small gray circles represent known alcoholic beverages used to train the machine learning models. The small black circles represent unknown alcoholic beverages (red wine, sweet potato shochu, and whiskey, herein). For known alcoholic beverages, prediction by machine learning was successful when the receptor layer material was C18-STNPs or phenyl-STNPs. Aminopropyl-STNPs or Vinyl-STNPs produced much larger prediction errors. Judging from these results, it seems to be important to use a hydrophobic receptor layer material in order to predict the alcohol concentration of alcoholic beverages. On the other hand, the performance of prediction about unknown alcoholic beverages was not still adequate even when the receptor layer material was C18-STNPs or Phenyl-STNPs. It should be emphasized herein that using machine learning and evaluating the prediction error allow for selection of the receptor layer material suitable for a target to be predicted. As described below with reference to FIGS. 13A to 13D (in the case of using nanoparticle receptor layers) and FIGS. 14A and 14B (in the case of using polymer receptor layers), the same results were confirmed even in a $N_2$ environment.

Figure 9:
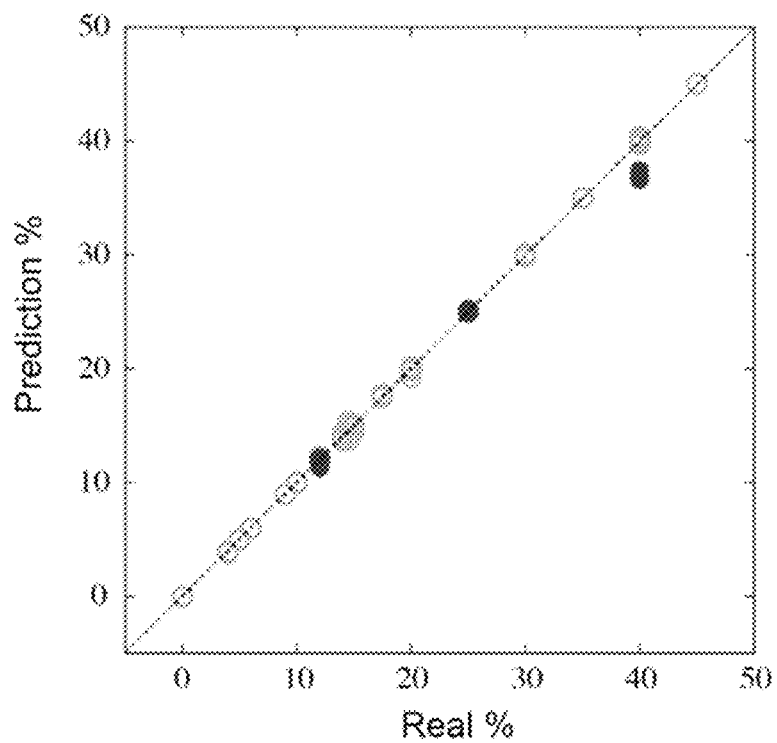
FIG. 9 is a diagram illustrating parity plots of predicted alcohol concentration (Prediction %) vs real alcohol concentration (Real %) in an atmospheric environment when parameter 3 of Phenyl-STNPs, parameter 4 of polysulfone, and parameters 1 and 3 of polycaprolactone were used. The small gray circles represent known alcoholic beverages used to train the machine learning model. The small black circles represent unknown alcoholic beverages (red wine (12%), sweet potato shochu (25%), and whiskey (40%)).

In order to further improve the prediction performance, examination was made for training of machine learning models using multiple signals obtained from a hydrophobic receptor layer material. In addition to C18-STNPs and Phenyl-STNPs, two types of commercially available hydrophobic polymers, that is, polysulfone and polycaprolactone (denoted by polysulfone and polycaprolactone in the drawings and tables, respectively) were used. With reference to FIGS. 15A, 15B, 16A, and 16B, a description is given of responses measured and training results when these polymers were used. Herein, the feature of signals by each polymer is also represented with the aforementioned four parameters, and the four channels of the sensor array provided 16 parameters. The machine learning models to predict the alcohol concentration of alcoholic beverages were constructed for all the combinations of the 16 parameters. The number of the trained machine learning models was therefore 65535 (=$2^{16}$−1). By performing 24-fold cross-validation, the prediction error Δ was evaluated for all of the aforementioned combinations, and the optimal combination was found. The prediction error Δ was 0.4315 for the optimal combination using Parameter 3 of MSS using Phenyl-STNPs, Parameter 4 of MSS using polysulfone, and Parameters 1 and 3 of MSS using polycaprolactone. This indicates that the prediction performance was drastically improved compared with that in the case of using a single receptor layer. FIG. 9 illustrates a parity plot of predicted alcohol concentration vs real alcohol concentration when the optimal combination was used. In FIG. 9, similarly to the parity plots in the lower side of FIG. 8, the small gray circles represent known alcoholic beverages used in machine learning. The small black circles represent unknown alcoholic beverages. FIG. 9 therefore revealed that prediction by machine learning models was successful not only for the known alcoholic beverages but also for the unknown alcoholic beverages with a high accuracy. This fact indicates that machine learning is one of powerful tools to find the quantity of a measuring target from multiple signals obtained through measurement with a chemical sensor represented by MSS.

Finally, Table 2 illustrates the appearance rate of each parameter in the top 100 combinations of parameters when the combinations of parameters are arranged in ascending order of the prediction errors when four MSS channels in the sensor array were used.

Table 2: Appearance Rate of Each Parameter in Top 100 Parameter Combinations when Four Channels were Used

TABLE 2

|  | C18 | Phenyl | Polysulfone | Polycaprolactone |
|---|---|---|---|---|
| Parameter 1 | 17% | 10% | 74% | 90% |
| Parameter 2 | 0% | 0% | 36% | 2% |
| Parameter 3 | 58% | 52% | 63% | 47% |
| Parameter 4 | 39% | 47% | 79% | 66% |

The prediction errors Δ by the top 100 combinations distributed between 0.4315 and 0.5735. Table 2 shows that the appearance rate of Parameter 2 was small, except for the case of polysulfone. The correlation of Parameter 2 with the alcohol concentration was exhibited only in the case of polysulfone as described later. In the cases of C18-STNPs and Phenyl-STNPs, the appearance rate of Parameter 3 is greater than that of Parameter 1. Polysulfone and polycaprolactone produced the opposite results thereto. These results suggest that nanoparticle coating extracts more information from the desorption process than from the adsorption process while those polymers have opposite tendencies. To interpret the tendencies, it is necessary to examine physicochemical properties of the nanoparticles and polymers. It is reported that one of the major factors that determine the shape of responses is the ratio of sorption and diffusion time constant. Nanoparticle coatings certainly include numerous pores formed by gaps between the nanoparticles. Such a porous structure contributes to faster sorption than that of polymer. It is therefore difficult to draw more information from the sorption process under the aforementioned parameter extraction conditions. On the other hand, the behavior of desorption will be the same as desorption from capillaries. Herein, in the case of a typical mesoporous material with a pore size ranging from 2 to 50 nm, hysteresis is normally observed. The retarded desorption should provide more information in the form of Parameter 3. Since polymers have a denser structure than the nanoparticle-based porous structure of polymers, both sorption and desorption to and from polymers take longer time. The information useful for prediction was therefore obtained from both of Parameters 1 and 3. The interaction between the receptor layer coating and adsorption properties also obviously influence the results discussed here.

(Details of Examples)

<Microfluidic Synthesis of Variously Functionalized Silica/Titania Hybrid Nanoparticles>

1.1 Chemicals

The following chemicals were used: tetraethoxysilane (TEOS, Tokyo Chemical Industry Co., Ltd), triethoxyvinylsilane (TEVS, Tokyo Chemical Industry Co., Ltd.), octadecyltriethoxysilane (ODTES, Tokyo Chemical Industry Co., Ltd.), trimethoxyphenylsilane (TMPS, Tokyo Chemical Industry Co., Ltd.), titanium tetraisopropoxide (TTIP, Tokyo Chemical Industry Co., Ltd.), isopropyl alcohol (IPA, Wako Pure Chemical Corporation), 28% ammonia aqueous solution ($NH_3$aq, KANTO CHEMICAL CO., INC.), octadecylamine (ODA, Aldrich, Inc.), and 3-aminopropyltriethoxy silane (APTES, Sigma, Inc.). These obtained chemicals were used as obtained.

1.2 Experimental Procedure

Silica/titania hybrid nanoparticles with various types of surface functionalization were synthesized using a multistep nucleation controlled growth method reported before, with some modifications added thereto. Briefly described, five types of starting solutions (solutions A to E) were prepared. The compositions of these solutions are summarized in Table 3.

Table 3: Amount of Chemicals Used to Synthesize Various Functionalized Nanoparticles

TABLE 3

| Solution A | | Solution B | | | Solution C | | Solution D | | Solution E | | |
|---|---|---|---|---|---|---|---|---|---|---|---|
| *1 (mL) | IPA (g) | $NH_{3aq}$ (g) | $H_2O$ (g) | IPA (g) | TTIP (mL) | IPA (g) | $H_2O$ (mL) | IPA (g) | ODA (g) | $H_2O$ (mL) | IPA (g) |
| *2 | *3 | 0.758 | 2.84 | 6.98 | 0.458 | 9.44 | 0.078 | 9.74 | 0.1368 | 40 | 123.3 |

Herein, *1-*3 in Table 3 are as follows:

*1
Aminopropyl-STNPs -> APTES
Vinyl-STNPs -> TEVS
C18-STNPs -> ODTES
Phenyl-STNPs -> TMPS

*2
Aminopropyl-STNPs -> 1.481
Vinyl-STNPs -> 1.330
C18-STNPs -> 2.000
Phenyl-STNPs -> 1.160

*3
Aminopropyl-STNPs -> 8.639
Vinyl-STNPs -> 8.757
C18-STNPs -> 8.232
Phenyl-STNPs -> 8.890

Using a syringe pump (CXN1070, a product of ISIS CO., Ltd.), solutions A to D were caused to individually flow through a perfluoroalkoxy alkane (PFA) tube (inner diameter, 1.0 mm; outer diameter, 1/16 inch; a product of YMC CO., LTD.) at 10 mL/min. Solutions A and B or solutions C and D were mixed in a polytetrafluoroethylene (PTFE) fluid channel provided with a Y-shaped connector (KeyChem mixer with a flow channel sectional area of about 1 mm2; a product of YMC CO., LTD.). The resultant two reaction solutions, that is, solution A+B and solution C+D were mixed in a second fluid channel subsequent to the two fluid channels. The first and second fluid channels were connected with a 10 cm long PFA tube. The mixture of the four types of solutions A to D was flowed through a 70 cm long PFA tube to be added to solution E being magnetically stirred. After the addition, the final reaction solution was aged for 24 hours at room temperature. Thus, slightly-opaque suspension was obtained.

1.3 Measurement

Using Nicolet 4700 FT-IR spectrometer (Thermo Fisher Scientific Inc.), Fourier transform infrared (FT-IR) spectra were measured with a resolution of 2.0 $cm^{-1}$. In this measurement, specimen powder and KBr were homogeneously mixed, and the mixture was pressed into a KBr disk for transmittance measurement.

Using Hitachi ultra-high resolution scanning electron microscope SU8000, scanning electron microscope (SEM) images were obtained with an acceleration voltage of 10 kV. Each specimen was coated with platinum to a thickness of several nanometers before measurement.

2. Spray Coating of Various Nanoparticles on MSS

Manufacturing of MSS themselves is the matter already known, and Patent Literature 1 and Non-patent literature 2 should be referred to, for example. The MSS surfaces were spray-coated with the four types of nanoparticle suspensions obtained as described above, by using a spray coating machine (rCoater, a product of ASAHI SUNAC CORPORATION). In the process of preparing the nanoparticle suspensions, every type of functionalized nanoparticles was centrifuged at 9000 rpm for 10 minutes. The deposit thereof was carefully washed with IPA for several times and was then added with an IPA/water mixture (the mixture ratio is 3 to 5 (volume ratio)). The concentration of the four types of suspensions was set at about 1 g/L. Prior to spray coating, the suspension was adequately ultrasonicated, so that the nanoparticles were dispersed as much as possible (some aggregates were still identified).

Next, the suspension was put into a syringe and was then caused to flow through a PTFE tube at a flow rate of 3 mL/min using a syringe pump (YSP-201, a product of YMC CO., LTD.). The suspension was introduced into a spray nozzle to be formed into uniform minute droplets using two types of carrier air (atomizing air, 0.030 MPa; patterning air, 0.030 MPa). A sensor array including four MSS was placed on the stage. The stage was heated at about 100° C. for quick evaporation of the minute droplets. The stage was moved back and forth while the spray nozzle was moved from left to right at 15 mm/min with 0.3 mm pitch. The distance between the spray nozzle and stage was set at 100 mm. This coating process was repeated to a coating thickness of about 1 μm. To prevent cross-contamination, a mask is used to cover three of the channels while coating was performed for the other one.

3. Detection Experiment 3.1 Specimen Liquid

Prior to experiments using alcoholic beverages, outputs of the aforementioned coated MSS on the sensor array in response to the 15 types of specimen liquids below were measured:

Formaldehyde solution (35 to 38%), n-hexane, ethanol, isopropyl alcohol, 1-butanol, 1-pentanol, benzene, toluene, xylene, 2-butanon, acetic acid, trichloromethane, and N,N-dimethylformamide; purchased from Wako Pure Chemical Corporation methanol, ethyl acetate, and tetrahydrofuran; purchased from KANTO CHEMICAL CO., INC.

n-heptane, n-octane, n-nonane, n-decan, n-undecane, and n-dodecane; purchased from Nacalai tesque co., ltd.

1,2-dichlorobenzene and acetone; purchased from Sigma-Aldrich Japan 1,3-dichlorobenzene; purchased from Aldrich Inc.

All these chemicals were used as purchased.

For quantitative measurement of alcohol concentration, specimens below were used. The alcohol concentration (which is called "alcohol percentage", indicating a volume concentration of ethanol) is shown in brackets below: Ultrapure water (0%), commercially-available water (0%), tap water (0%), phosphate buffered saline (0%), green tea (0%), oolong tea (0%), shochu & green tea (4%), beer (5%), shochu & oolong tea (6%), sangria (9%), umeshu (12%), red wine (12%), cooking sake (14%), mirin (14.5%), Japanese sake (15%), Shaoxing wine (17.5%), barley shochu (20%), cassis liqueur (20%), plant worm shochu (25%), sweet potato shochu (25%), vodka (40%), gin (40%), palinka (40%), rum (40%), brandy (40%), and whisky (40%) (in the drawings, respectively denoted by Ultrapure water, Commercial water, Tap water, PBS, Green tea, Oolong tea, Shochu & Green tea, Beer, Shochu & Oolong tea, Sangria, Umeshu, Red wine, Ryorishu, Mirin, Japanese sake, Shokoshu, Shochu (barley), Cassis liqueur, Shochu (plant worm), Shochu (sweet potatoes), Vodka, Gin, Palinka, Rum, Brandy, and Whisky). In addition, water and ethyl alcohol mixture of various concentrations were used (the mixture ratio was: 95/5; 90/10; 85/15; 80/20; 75/25; 70/30; 65/35; 60/40; and 55/45) (in the drawings, respectively denoted by 95/5 Water/EtOH, 90/10 Water/EtOH, 85/15 Water/EtOH, 80/20 Water/EtOH, 75/25 Water/EtOH, 70/30 Water/EtOH, 65/35 Water/EtOH, 60/40 Water/EtOH, and 55/45 Water/EtOH).

3.2 Detailed Procedure and Condition of Detection Experiment

In the experiments of Examples, a sensor array including MSS functionalized with various types of nanoparticles was mounted in a chamber, and the chamber was carefully sealed with an O-ring. Using two piezoelectric pumps, outside air was introduced into the chamber at a flow rate of 14 mL/min. One of the pumps was used for purging, that is, accelerating desorption of the adsorption material, and the other pump was used to introduce the specimen vapor with air. Herein, a predetermined amount of the liquid specimen was put in a small vial covered with a rubber lid, and a hollow needle connected to a PTFE tube was stuck into the head space of the vial through the rubber lid. The other end of the PTFE tube was connected to the piezoelectric pump so that the specimen vapor was drawn out of the head space. Another hollow needle connected to another PTFE tube with the other end open to air was stuck into the head space to allow the fluid to flow smoothly. The two piezoelectric pumps were switched every 10 seconds to repeat the cycle of specimen introduction and purging. This cycle was repeated five times. Voltage of −1 V was applied to MSS as bridge voltage, and outputs from MSS were obtained (as well known, four piezoresistive elements are provided for detection of surface stress on MSS and are connected to form a bridge circuit. The bridge voltage is applied across two terminals of the bridge circuit opposite to each other while the voltage across the other two terminals is obtained as a detection output. Patent Literature 1 and Non-patent Literature 1, for example, should be referred to for details.). The output voltage from MSS was sampled with 20 Hz. All the experiments were conducted under atmospheric conditions without controlling temperature and pressure.

4. Kernel Ridge Regression

Kernel ridge regression (KRR) is one of the powerful machine learning methods to predict unknown data from a known data set. KRR itself is the matter known by those skilled in the art, and the detail thereof is not described. Hereinafter, a description is given of a process of machine learning using KRR in Examples.

N data sets $$\{X_n, A(X_n)\}_{n=1,\ldots,N} \qquad \text{[MATH. 2]}$$

are given. Herein $$X_n \qquad \text{[MATH. 3]}$$

represents a vector in which the elements are parameters extracted from a signal measured as odor of an alcoholic beverage labeled "n" in Examples.

$$A(X_n) \qquad \text{[MATH. 4]}$$

represents the alcohol concentration of the alcoholic beverage. Herein, it should be noted that the dimension of $$X_n \qquad \text{[MATH. 5]}$$

depends on the number of parameters and the number of MSS channels. The alcohol concentration $$A^*(X^*) \qquad \text{[MATH. 7]}$$

of an unknown alcoholic beverage including a parameter (extracted from a signal obtained by measuring an unknown alcohol liquid)

$$X^* \qquad \text{[MATH. 6]}$$

is predicted by KRR as

[MATH. 8]

$$A^*(X^*) = k^T(K+\lambda I)^{-1}A \qquad (5)$$

Herein,

[MATH. 9]

$$A = (A(X_1) \ldots A(X_N))^T, \qquad (6)$$

$$k = (k(X_1, X^*) \ldots k(X_N, X^*))^T, \qquad (7)$$

$$K = \begin{pmatrix} k(X_1, X_1) & \cdots & k(X_1, X_N) \\ \vdots & \ddots & \vdots \\ k(X_N, X_1) & \cdots & k(X_N, X_N) \end{pmatrix}. \qquad (8)$$

In addition, $$I \qquad \text{[MATH. 10]}$$

is an N×N unit vector, and $$k(X_n, X_m) \qquad \text{[MATH. 11]}$$

is a kernel function representing the similarity between $$X_n \qquad \text{[MATH. 12]}$$

and $$X_m. \qquad \text{[MATH. 13]}$$

Herein, the following Gaussian kernel is used.

[MATH. 14]

$$k(X_n, X_m) = \exp\left[-\frac{1}{2\sigma^2}|X_n - X_m|^2\right] \qquad (9)$$

In this procedure, λ and σ are hyperparameters to be given prior to the analysis. The prediction performance greatly depends on the values of the hyperparameters.

In the machine learning field, there are various regression methods, and it should be noted that the regression method in Examples of the application is just an example.

5. Cross Validation

To determine the values of the hyperparameters λ and σ in KRR, cross validation was used. Cross validation is also the matter known by those skilled in the art, and the detail thereof is not described herein. To be brief, part of data is removed from the data set before training, and the removed data is regarded as test data and is used to validate the prediction. Cross validation error is calculated as a representation of the prediction error. The values of the hyperparameters are evaluated so as to minimize the cross validation error. The following illustrates the procedure of S-fold cross validation.

First, a data set D including N sets of data was divided into S data subsets at random. Each data subset is indicated by $D_s$. Herein, s=1, ..., S, and the number of sets of data in each data subset is N/S. One of the S data subsets is regarded as the test data, and the other S−1 data subsets are used as the training data. The number of sets of test data and the number of sets of training data are $N_{te}$=N/S and $N_{tr}$=N (S−1)/S.

Next, each data subset $G_s$=D$D_s$ composed of $N_{tr}$ set of data is subjected to KRR while λ and σ are varied. For the parameter $$X,$$ [MATH. 15]

the prediction $$A^{*(s)}(X;\lambda,\sigma)$$ [MATH. 16]

of alcohol concentration depending on the hyperparameters λ and σ is obtained. The mean square deviation between the alcohol concentration of the test data $D_s$ and the predicted alcohol concentration

[MATH. 17]

$$\Delta^{(s)}(\lambda, \sigma) = \frac{1}{N_{te}} \sum_{l \in D_s} [A(X_l) - A^{*(s)}(X_l; \lambda, \sigma)]^2 \quad (10)$$

is calculated.

Furthermore, averaging S different mean square deviations produces cross validation error depending on λ and σ. This value is as follows.

[MATH. 18]

$$\Delta(\lambda, \sigma) = \frac{1}{S} \sum_{s=1}^{S} \Delta^{(s)}(\lambda, \sigma) \quad (11)$$

By minimizing the value of Δ(λ, σ) with respect to λ and σ, optimal values λ* and σ* of the hyperparameters are evaluated. These values implement good prediction. Lastly, the prediction error of machine learning that represents the prediction performance is defined as:

[MATH. 19]

$$\Delta = \Delta(\lambda^*, \sigma^*) \quad (12)$$

This prediction error was used to search for the optimal combination of parameters extracted from the signal and the receptor layer material to predict the alcohol concentration of alcoholic beverage in Examples.

There are various methods to determine hyperparameters in machine learning models, and the prediction error is variously defined. It should thus be noted that the machine learning method described above is just an example.

[Polymer Receptor Layer Material]

As described above, the receptor layer material can further include a polymer or another material in addition to the nanoparticles. The following illustrates additional data when the above-described two types of polymers, that is, polysulfone and polycaprolactone, were used.

Figure 17A:
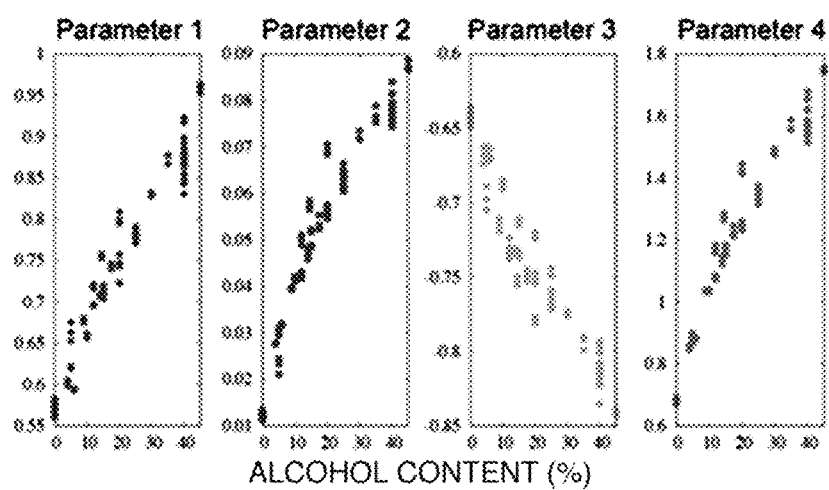
FIG. 17A is a diagram illustrating alcohol concentration dependence of parameters extracted from signals measured in an atmospheric environment. Each graph includes 105 data points.
Figure 17A:
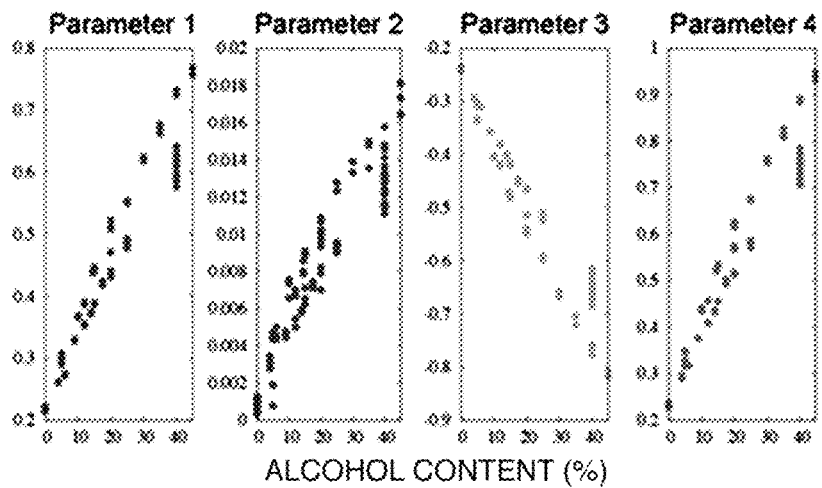
Figure 17B:
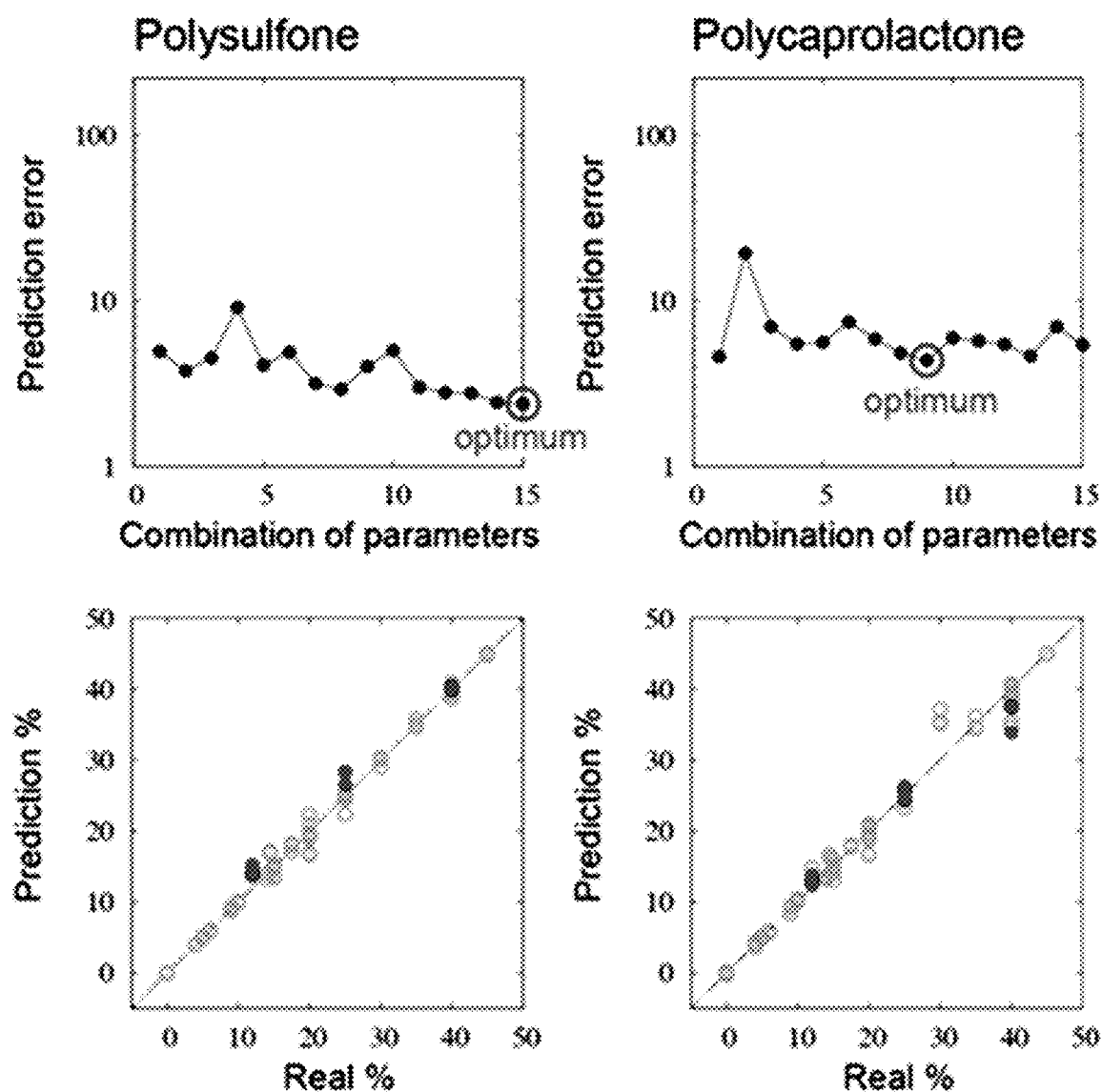
In FIG. 17B, upper diagrams illustrate dependence of prediction error on the combination of four parameters extracted from signals measured in an atmospheric environment. Numerical values indicating the combination of parameters in decimal notation are defined in the same manner as in the case of FIG. 8. Lower diagrams illustrate parity plots of predicted alcohol concentration to real alcohol concentration in an atmospheric environment. The small gray circles represent known alcoholic beverages used to train the machine learning model. The small black circles represent unknown alcoholic beverages (red wine (12%), sweet potato shochu (25%), and whiskey (40%)). The indications on the vertical and horizontal axes are the same as those of FIG. 8.

FIG. 17A illustrates alcohol concentration dependence of parameters extracted from signals obtained by measuring the 35 types of alcoholic beverages with MSS when polysulfone and polycaprolactone were used as the receptor layer material. In this case, a certain degree of correlation was confirmed between the alcohol concentration and all parameters 1 to 4. FIG. 17B and Table 4 illustrate the results of training under atmospheric conditions when polysulfone and polycaprolactone were used as the receptor layer material. It was assumed that the various settings were completely the same as those in the case of the receptor layer. As for known alcoholic beverages, the machine learning models using receptor layers both produced good results.

Table 4: Optimal Combination of Parameters and Optimal Prediction Error Depending on Sensitive Membrane Material Under Atmospheric Conditions

TABLE 4

|  | Polysulfone | Polycaprolactone |
| --- | --- | --- |
| Parameter 1 | ✓ | ✓ |
| Parameter 2 | ✓ | — |
| Parameter 3 | ✓ | — |
| Parameter 4 | ✓ | ✓ |
| Prediction error | 2.3757 | 4.3535 |

[Case in $N_2$ Environment]

The above description is premised on the behavior of the receptor layer in the atmosphere. The following description illustrates the results of prediction by machine learning when the experiments were conducted in $N_2$ instead of in the atmosphere.

For quantitative measurement of alcohol concentration in a $N_2$ environment, following specimens were used. The alcohol concentration is shown in brackets below:

Ultrapure water (0%), beer (5%), sangria (9%), umeshu (12%), red wine (12%), cooking sake (14%), mirin (14.5%), Japanese sake (15%), Shaoxing wine (17.5%), barley shochu (20%), cassis liqueur (20%), plant worm shochu (25%), sweet potato shochu (25%), vodka (40%), gin (40%), palinka (40%), rum (40%), brandy (40%), and whisky (40%) (in the drawings, respectively denoted by Ultrapure water, Beer, Sangria, Umeshu, Red wine, Ryorishu, mirin, Japanese sake, Shokoshu, Shochu (barley), Cassis liqueur, Shochu (plant worm), Shochu (sweet potatoes), Vodka, Gin, Palinka, Rum, Brandy, and Whisky). In addition, water and ethyl alcohol mixture of various concentrations were used (the mixture ratio was: 80/20 and 60/40) (in the drawings, respectively denoted by 80/20 Water/EtOH and 60/40 Water/EtOH).

<Case of Using Nanoparticles>

Figure 18A:
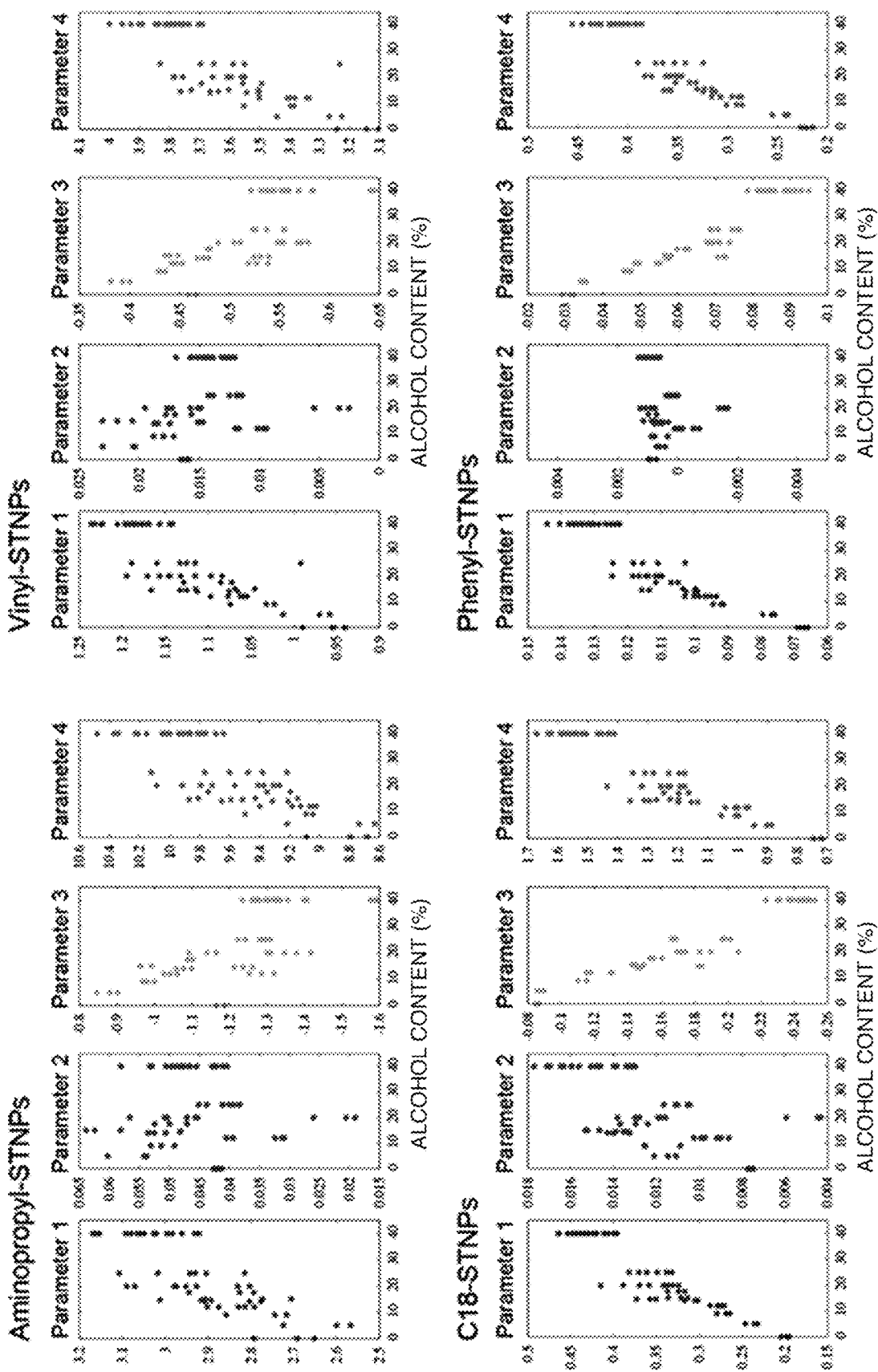
FIG. 18A is a diagram illustrating alcohol concentration dependence of parameters extracted from signals measured under $N_2$ conditions. Each graph includes 63 data points.
Figure 18B:
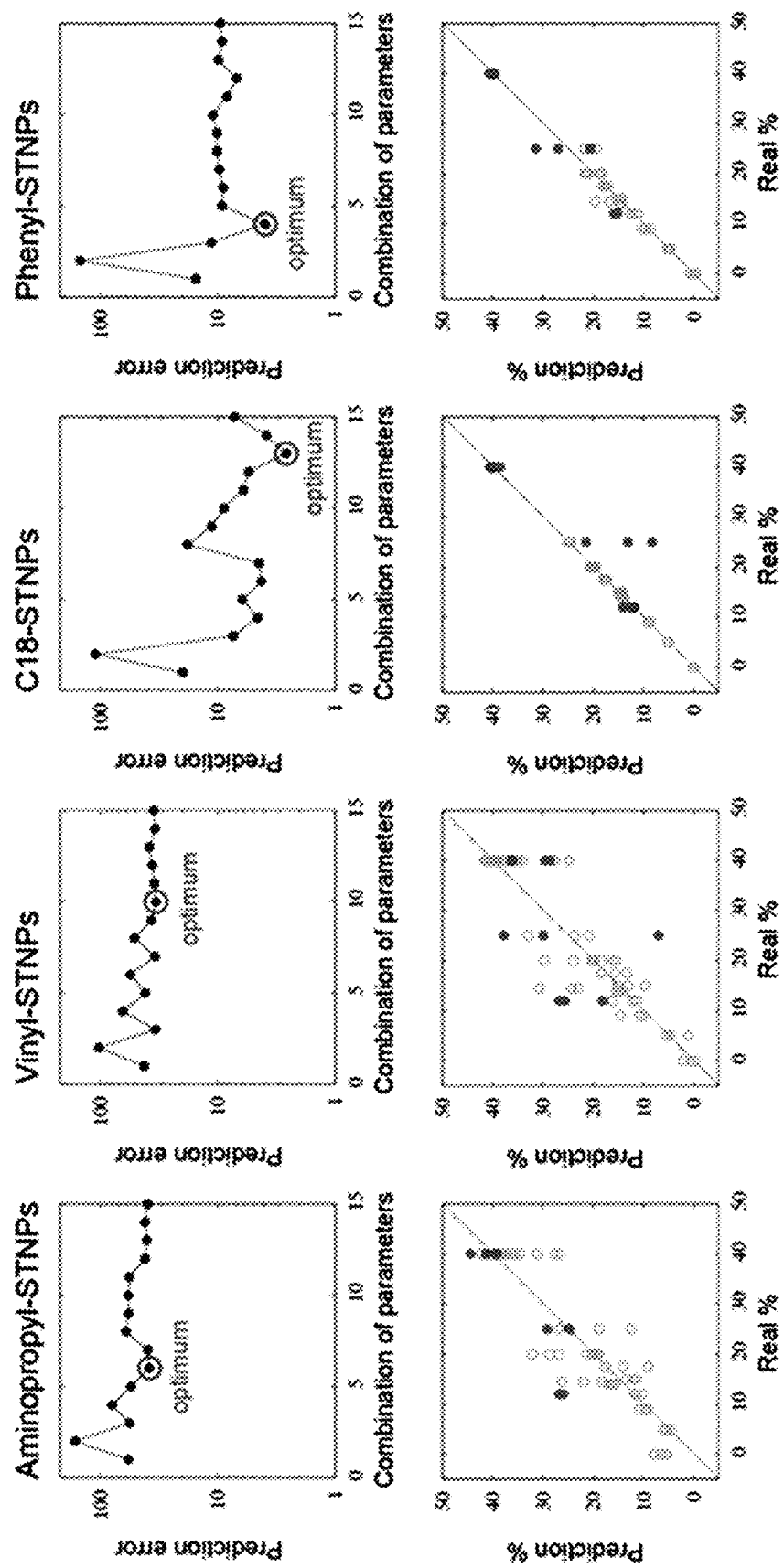
In FIG. 18B, upper diagrams illustrate dependence of prediction error on the combination of four parameters extracted from signals measured under $N_2$ conditions. Numerical values in decimal notation indicating combinations of parameters are defined in the same manner as in the case of FIG. 8. Lower diagrams illustrate parity plots of predicted alcohol concentration vs real alcohol concentration in a $N_2$ environment. The small gray circles represent known alcoholic beverages used to train the machine learning model. The small black circles represent unknown alcoholic beverages (red wine (12%), sweet potato shochu (25%), and whiskey (40%)).

FIG. 18A illustrates alcohol concentration dependence of the parameters extracted from signals in the measurements of the 21 types of alcoholic beverages with MSS using the aforementioned four types of nanoparticle receptor layer material used in above Examples, that is, Aminopropyl-STNPs, Vinyl-STNPs, C18-STNPs, and Phenyl-STNPs. Parameters 1 to 4 were extracted using Formulae (1) to (4) previously illustrated. Herein, $t_b=t_a+3$ (sec), $t_c=t_a+30$ (sec), and $t_d=t_a+33$ (sec). For each alcoholic beverage, three peaks at $t_a=90$, 150, and 210 were used. Each graph of FIG. 18A includes 63 data points. It was confirmed that the parameters, except for Parameter 2, had a certain degree of correlation with the alcohol concentration. FIG. 18B and Table 5 illustrate the results of training in a $N_2$ environment when the receptor layer material was Aminopropyl-STNPs, Vinyl-STNPs, C18-STNPs, or Phenyl-STNPs. It was assumed that the various settings were completely the same as those under the atmospheric conditions. As for known alcoholic beverages, the machine learning models produced good results when the receptor layer material was C18-STNPs or Phenyl-STNPs. However, the machine learning models showed large prediction errors when the receptor layer material was Aminopropyl-STNPs and Vinyl-STNPs, similarly to the case under the atmospheric conditions.

Table 5: Optimal Combination of Parameters and Optimal Prediction Error Depending on Sensitive Membrane Material in a $N_2$ Environment

TABLE 5

|  | Aminopropyl | Vinyl | C18 | Phenyl |
|---|---|---|---|---|
| Parameter 1 | — | — | ✓ | — |
| Parameter 2 | ✓ | ✓ | — | — |
| Parameter 3 | ✓ | — | ✓ | ✓ |
| Parameter 4 | — | ✓ | ✓ | — |
| Prediction Error | 38.5028 | 33.7003 | 2.6086 | 3.9367 |

<Case of Using Polymers>

Figure 18C:
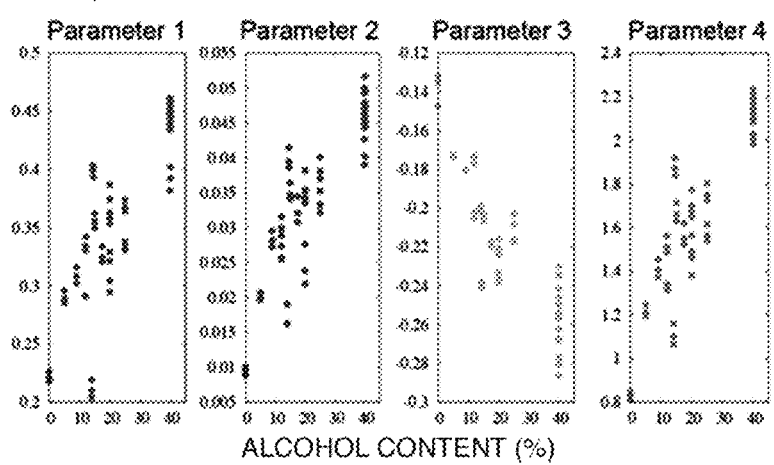
FIG. 18C is a diagram illustrating alcohol concentration dependence of parameters extracted from signals measured under $N_2$ conditions. Each graph includes 63 data points.
Figure 18C:
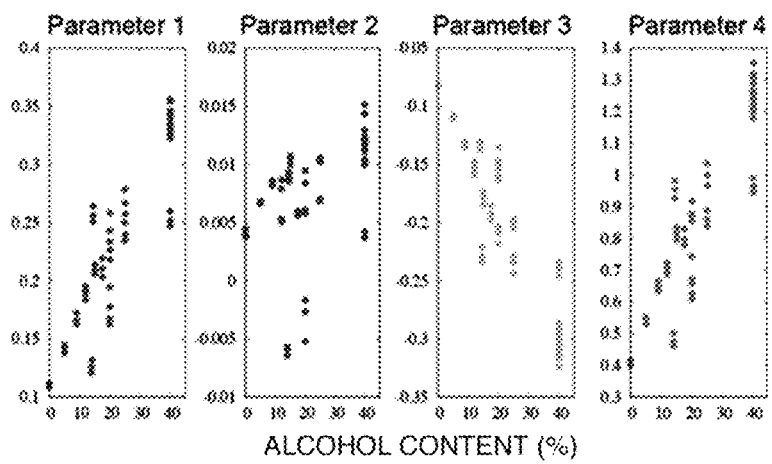
Figure 18D:
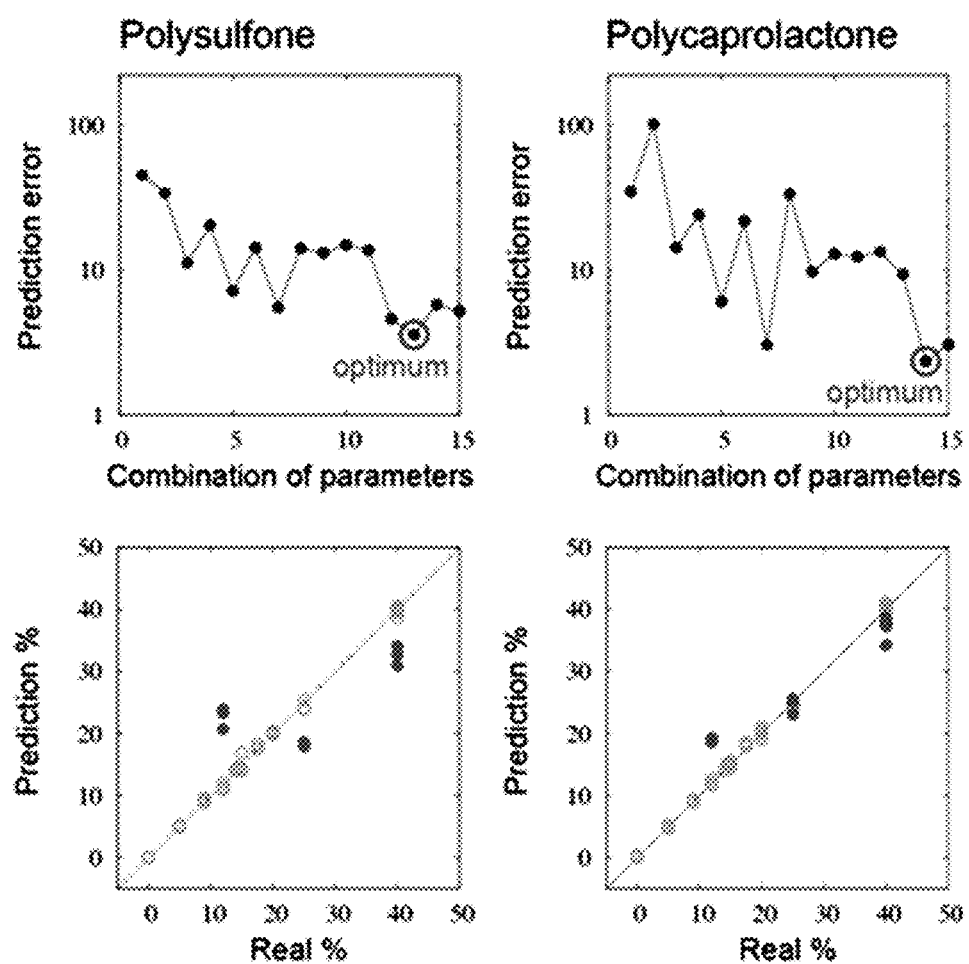
In FIG. 18D, upper diagrams illustrate dependence of prediction error on the combination of four parameters extracted from signals in a $N_2$ environment. Numerical values in decimal notation indicating combinations of parameters are defined in the same manner as in the case of FIG. 8. Lower diagrams illustrate parity plots of predicted alcohol concentration vs real alcohol concentration in a $N_2$ environment. The small gray circles represent known alcoholic beverages used to train the machine learning model. The small black circles represent unknown alcoholic beverages (red wine (12%), sweet potato shochu (25%), and whiskey (40%)). The indications on the vertical and horizontal axes are the same as those in FIG. 8.

FIG. 18C illustrates alcohol concentration dependence of parameters extracted from signals in the measurements of the 21 types of alcoholic beverages by MSS when polysulfone and polycaprolactone were used as the receptor layer material. In this case, a certain degree of correlation was confirmed between with the alcohol concentration and all Parameters 1 to 4. FIG. 18D and Table 6 illustrate the results of training under $N_2$ conditions when polysulfone and polycaprolactone were used as the receptor layer material. It was assumed that the various settings were completely the same as those in the atmosphere. As for known alcoholic beverages, the machine learning models using the receptor layers both produced good results.

Table 6: Optimal Combination of Parameters and Optimal Prediction Error Depending on Sensitive Membrane Material Under $N_2$ Conditions

TABLE 6

|  | Polysulfone | Polycaprolactone |
|---|---|---|
| Parameter 1 | ✓ | — |
| Parameter 2 | — | ✓ |
| Parameter 3 | ✓ | ✓ |
| Parameter 4 | ✓ | ✓ |
| Prediction Error | 3.5752 | 2.3476 |

INDUSTRIAL APPLICABILITY

The field to which the invention is applicable is certainly not limited to quantitative analyses of odor. The invention is applicable to any field in which it is useful to quantitatively detect a specific component out of gas or liquid that includes multiple components or possibly includes multiple components. By applying the invention to apparatuses which quantitatively analyze breath, sweat, saliva, tears, and other body fluids and gas and odor emitted from the body, for example, such apparatuses can be used in analyses and screening of diseases. In addition, the invention is expected to be widely used in all areas where the quantitative detection and analyses are useful, such as food manufacture, storage, distribution, and security or medicine fields.

The invention claimed is:

1. A method of estimating a specific estimation target value associated with a specific chemical component of an unknown specimen based on a result of machine learning learned from an output of an array of a plurality of chemical sensors, wherein chemical sensors in the array of the plurality of chemical sensors responds to at least one of the plurality of chemical components comprising the specific chemical component of the unknown specimen differently from each other, the method comprising:
   obtaining signal values at a plurality of selected time points in at least one cycle of each periodic variation of the output when an amount of a single specimen given to the plurality of chemical sensors is periodically varied, the single specimen being one of a plurality of known specimens having known values of the specific estimation target;
   extracting a plurality of parameters which represent a characteristic of a response of the plurality of chemical sensors from the obtained signal values at the plurality of selected time points for each of the plurality of known specimens;
   performing machine learning to obtain a relationship between the values of the specific estimation target and the characteristic of the response of the plurality of chemical sensors, based on differences in the plurality of parameters, without using a saturated value of the output;
   obtaining an output from the array of the plurality of chemical sensors for the unknown specimen; and
   estimating the specific estimation target value of the unknown specimen using the obtained relationship.

2. The method according to claim 1, wherein the amount of the single specimen given to the plurality of chemical sensors is periodically varied by periodically switching between a reference specimen and one of a plurality of known specimens to provide to the array of the plurality of chemical sensors.

3. The method according to claim 1, wherein the estimation target is a concentration of the specific chemical component of the specimen.

4. The method according to claim 1, wherein the array of the plurality of chemical sensors consists of a plurality of Membrane-type Surface stress Sensors (MSS) functionalized with receptor layers of different materials thereon.

* * * * *